US012674123B2

(12) United States Patent
Schäfer et al.

(10) Patent No.: US 12,674,123 B2
(45) Date of Patent: Jul. 7, 2026

(54) METHOD FOR 3D PRINTING OF VASCULARIZED TISSUES AND ORGANS

(71) Applicant: Technische Universität Berlin, Berlin (DE)

(72) Inventors: Konstanze Schäfer, Berlin (DE); Andreas Salomon, Berlin (DE)

(73) Assignee: Technische Universitat Berlin, Berlin (DE)

( * ) Notice: Subject to any disclaimer, the term of this patent is extended or adjusted under 35 U.S.C. 154(b) by 818 days.

(21) Appl. No.: 17/590,231

(22) PCT Filed: Aug. 3, 2020

(86) PCT No.: PCT/EP2020/071804
§ 371 (c)(1),
(2) Date: Feb. 1, 2022

(87) PCT Pub. No.: WO2021/023708
PCT Pub. Date: Feb. 11, 2021

(65) Prior Publication Data
US 2023/0399597 A1 Dec. 14, 2023

(30) Foreign Application Priority Data
Aug. 2, 2019 (EP) ..................................... 19189755

(51) Int. Cl.
*C12M 3/00* (2006.01)
*A61L 27/50* (2006.01)
(Continued)

(52) U.S. Cl.
CPC ........... *C12M 21/08* (2013.01); *A61L 27/507* (2013.01); *B29C 64/112* (2017.08);
(Continued)

(58) Field of Classification Search
CPC ... B29C 64/112; B29C 64/209; B29C 64/245; B29C 64/264; B29C 64/393;
(Continued)

(56) References Cited

U.S. PATENT DOCUMENTS

2003/0175410 A1* 9/2003 Campbell ............... A61L 27/38
623/23.72
2004/0253365 A1* 12/2004 Warren .................. C12M 33/00
118/715
(Continued)

FOREIGN PATENT DOCUMENTS

WO WO-2018035282 A1 * 2/2018 ........... B29C 64/112
WO 2019109127 A1 6/2019

OTHER PUBLICATIONS

Int'l Search Report issued for PCT/EP2020/071804, dated Dec. 14, 2020.
(Continued)

*Primary Examiner* — Jeffrey M Wollschlager
*Assistant Examiner* — Edgaredmanuel Troche
(74) *Attorney, Agent, or Firm* — MaxGoLaw PLLC

(57) ABSTRACT

The 3D printing method disclosed here for the production of vascularized tissues and organs requires a droplet printer to produce photorealistic high-resolution prints and a device for applying non-directional or directional electromagnetic waves. The process uses a new type of capillary ink that crosslinks or undergoes a layer-forming reaction only in the edge area of the ink drops. Unbound capillary ink components are removed. The resulting cavities form a capillary network with diameters of up to approx. 10 µm. Also disclosed is a novel printer table for supplying the printed tissue with medium during printing and a printer head supply unit for individually mixing the bio-inks from cell concentrate and various ink concentrates.

8 Claims, 20 Drawing Sheets ascending flushing
direction descending flushing
direction

(51) Int. Cl.

| | |
|---|---|
| *B29C 64/112* | (2017.01) |
| *B29C 64/209* | (2017.01) |
| *B29C 64/245* | (2017.01) |
| *B29C 64/264* | (2017.01) |
| *B29C 64/393* | (2017.01) |
| *B33Y 10/00* | (2015.01) |
| *B33Y 30/00* | (2015.01) |
| *B33Y 50/02* | (2015.01) |
| *B29L 31/00* | (2006.01) |

(52) U.S. Cl.

CPC .......... *B29C 64/209* (2017.08); *B29C 64/245* (2017.08); *B29C 64/264* (2017.08); *B29C 64/393* (2017.08); *B33Y 10/00* (2014.12); *B33Y 30/00* (2014.12); *B33Y 50/02* (2014.12); *B29L 2031/7532* (2013.01)

(58) Field of Classification Search

CPC ... B29C 64/343; B29C 64/106; B29C 64/124; B29C 64/30; B29C 64/135; B29L 2031/7532; C12M 21/08; A61L 27/507; A61L 27/3808; A61L 27/54; A61L 27/38; A61L 27/20; A61L 27/24; A61L 27/52; A61L 27/14; A61L 27/16; A61L 27/18; A61L 27/22; A61L 27/225; A61L 27/227; A61L 27/26; A61L 27/36; A61L 27/3604; A61L 27/3616; A61L 27/3625; A61L 27/3633; B33Y 10/00; B33Y 30/00; B33Y 50/02; B33Y 40/00; B33Y 80/00; B33Y 70/10; B33Y 70/00; C12N 2529/00; C12N 5/0062; C12N 5/069; C12N 2502/28; C12N 2537/10; B29K 2995/0056; B29K 2105/0061; B29K 2105/24; B29K 2995/006; A61F 2002/30985; C07K 5/1005; C07K 5/06034; C07K 5/06052; C07K 5/0808; C07K 5/101; C07K 7/06; C08J 2371/02; C08J 2389/06; C08J 3/075

USPC ....................................................... 264/401

See application file for complete search history.

(56) References Cited

U.S. PATENT DOCUMENTS

| | | | |
|---|---|---|---|
| 2010/0208006 A1* | 8/2010 | Selinfreund ....... | G01N 35/1016 347/68 |
| 2011/0076734 A1 | 3/2011 | Zhou et al. | |
| 2015/0217514 A1* | 8/2015 | Maier .................. | B29C 64/112 264/241 |
| 2020/0384690 A1* | 12/2020 | Myers ................... | C12M 21/08 |

OTHER PUBLICATIONS

Office Action issued in corresponding Australian Appln. No. 2020324525, dated Jun. 16, 2025.

* cited by examiner

*Figure 1*

Schematic printer structure

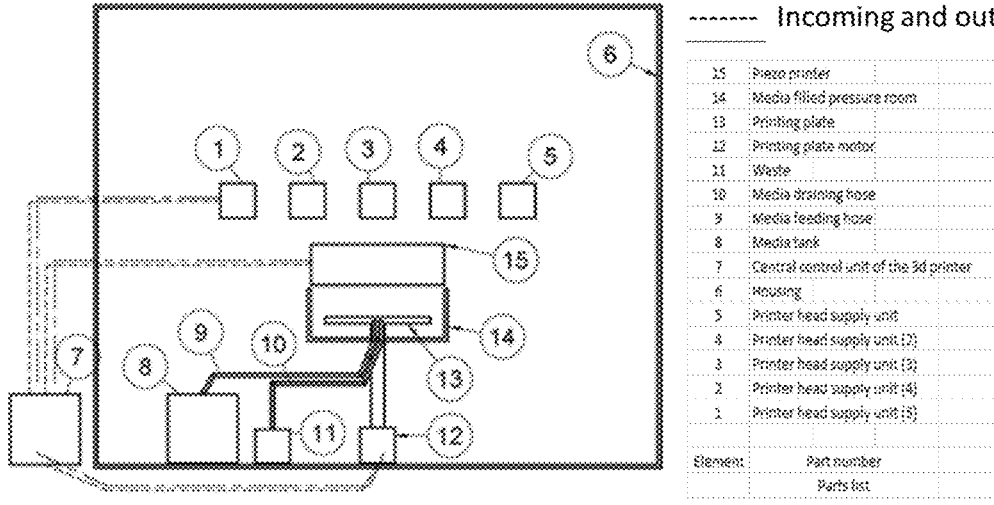

------- Incoming and outgoing signals

| Element | Part number |
| --- | --- |
| 15 | Piezo printer |
| 14 | Media filled pressure room |
| 13 | Printing plate |
| 12 | Printing plate motor |
| 11 | Waste |
| 10 | Media draining hose |
| 9 | Media feeding hose |
| 8 | Media tank |
| 7 | Central control unit of the 3d printer |
| 6 | Housing |
| 5 | Printer head supply unit |
| 4 | Printer head supply unit (2) |
| 3 | Printer head supply unit (3) |
| 2 | Printer head supply unit (4) |
| 1 | Printer head supply unit (5) |
| Element | Part number |
|  | Parts list |

| Element | Part number |
|---------|-------------|
| 10 | Silicone mat |
| 9 | Pressure chamber wall (frame) |
| 8 | Base plate for pressure chamber |
| 7 | Printing plate |
| 6 | Printer table |
| 5 | Printer table foot |
| 4 | Magnetic plate |
| 3 | Step motor |
| 2 | Micrometer screw |
| 1 | Medium inlet and outlet |
| | Parts list |

*Figure 3*
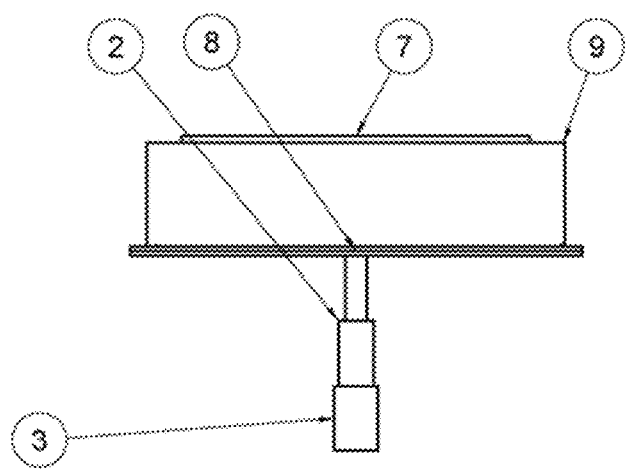
| 10 | Silicone mat |
| 9 | Pressure chamber wall (frame) |
| 8 | Base plate for pressure chamber |
| 7 | Printing plate |
| 6 | Printer table |
| 5 | Printer table foot |
| 4 | Magnetic plate |
| 3 | Step motor |
| 2 | Micrometer screw |
| 1 | Medium inlet and outlet |
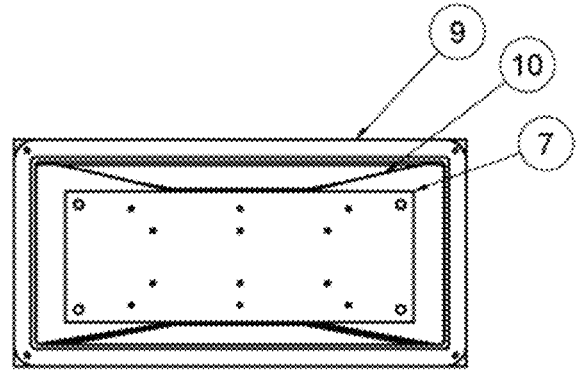

*Figure 4*
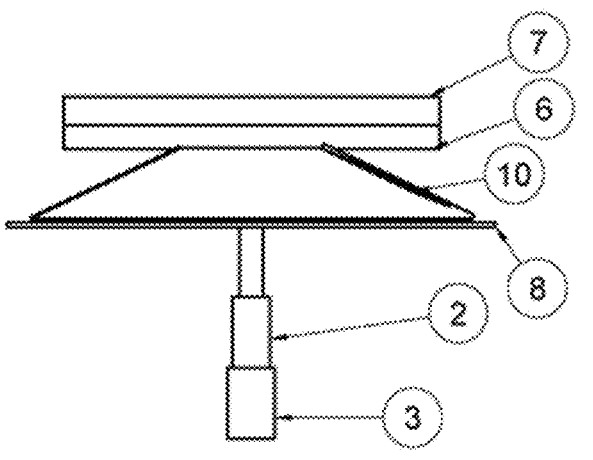
| 10 | Silicone mat |
| 9 | Pressure chamber wall (frame) |
| 8 | Base plate for pressure chamber |
| 7 | Printing plate |
| 6 | Printer table |
| 5 | Printer table foot |
| 4 | Magnetic plate |
| 3 | Step motor |
| 2 | Micrometer screw |
| 1 | Medium inlet and outlet |
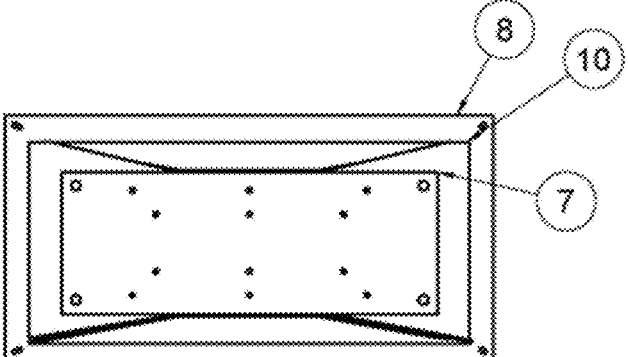

| 10 | Silicone mat |
|----|--------------|
| 8 | Base plate for pressure chamber |
| 7 | Printing plate |
| 6 | Printer table |
| 3 | Step motor |

*Figure 6*
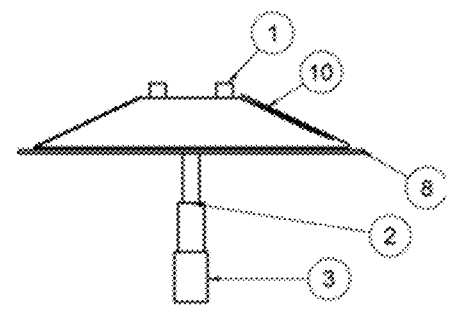
| 10 | Silicone mat |
| --- | --- |
| 8 | Base plate for pressure chamber |
| 3 | Step motor |
| 2 | Micrometer screw |
| 1 | Medium inlet and outlet |
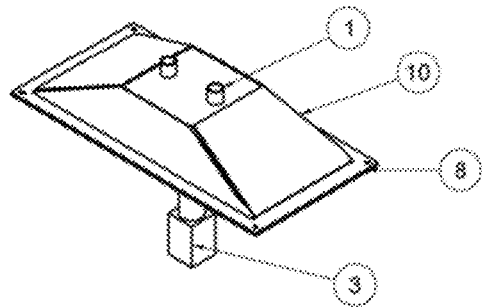

| 7 | Printer plate |
|---|---|
| 1 | Medium inlet and outlet |

Printhead supply unit

| 12 | Ink supply |
| 11 | Piezo print head |
| 10 | Cell counter |
| 9 | Discharge hose (ink) |
| 8 | Cell counter |
| 7 | Mixing unit |
| 6 | Cell concentrator |
| 5 | Pump (1) |
| 4 | Pump |
| 3 | Enclosure |
| 2 | Cell tank |
| 1 | Container for ink concentrate |

Decanter

Figure 13
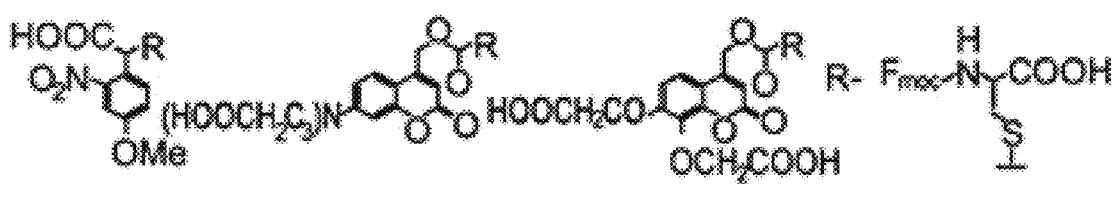
2 (C4MNB)     15 (BCMACMOC)     16 (78BCMCMOC)
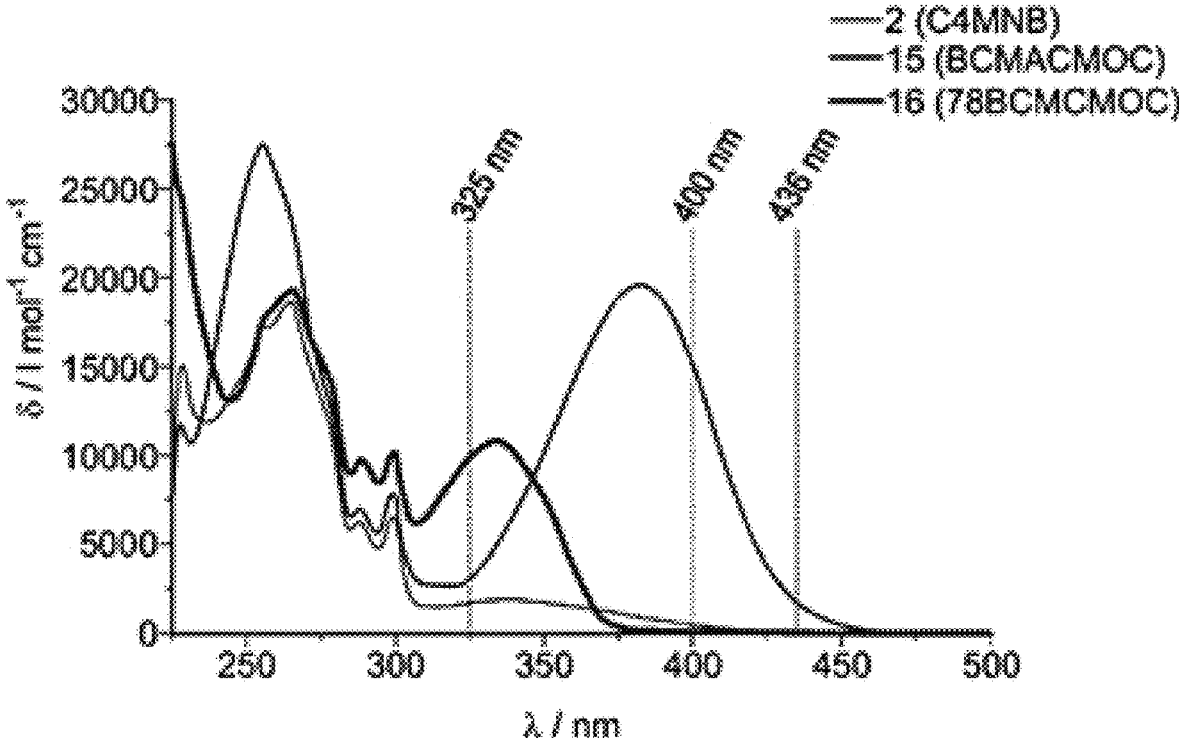

*Figure 16*
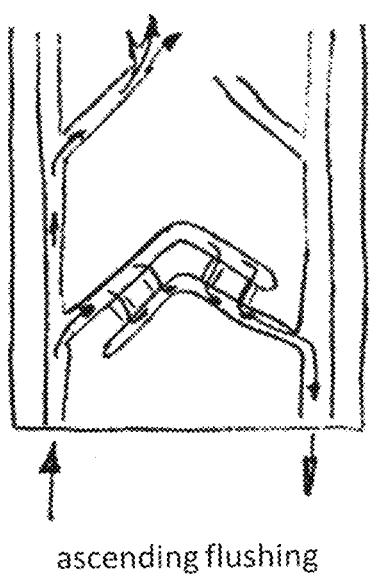
ascending flushing
direction
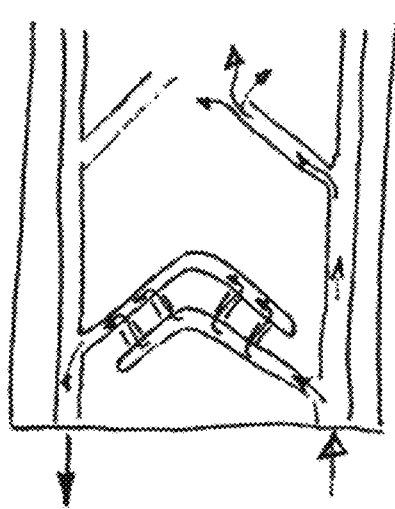
descending flushing
direction Figure 17A
Figure 17B
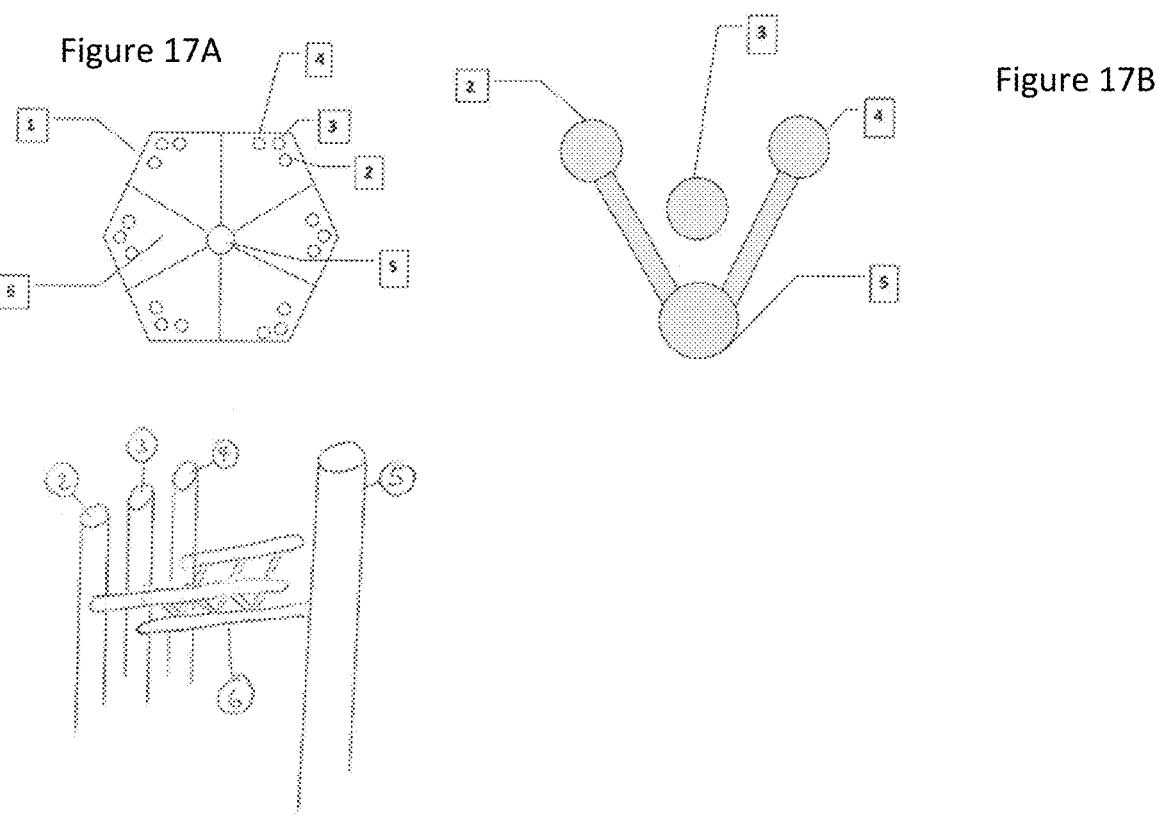
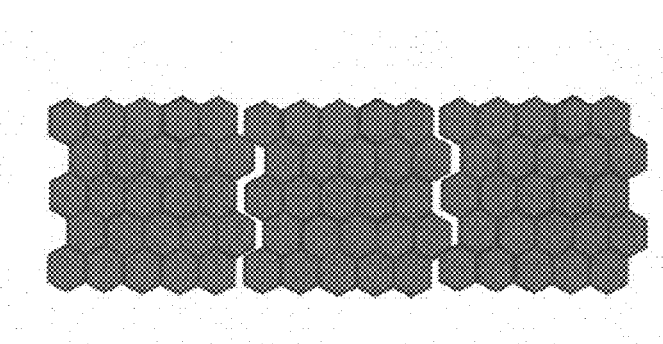
Figure 17C
Figure 17D

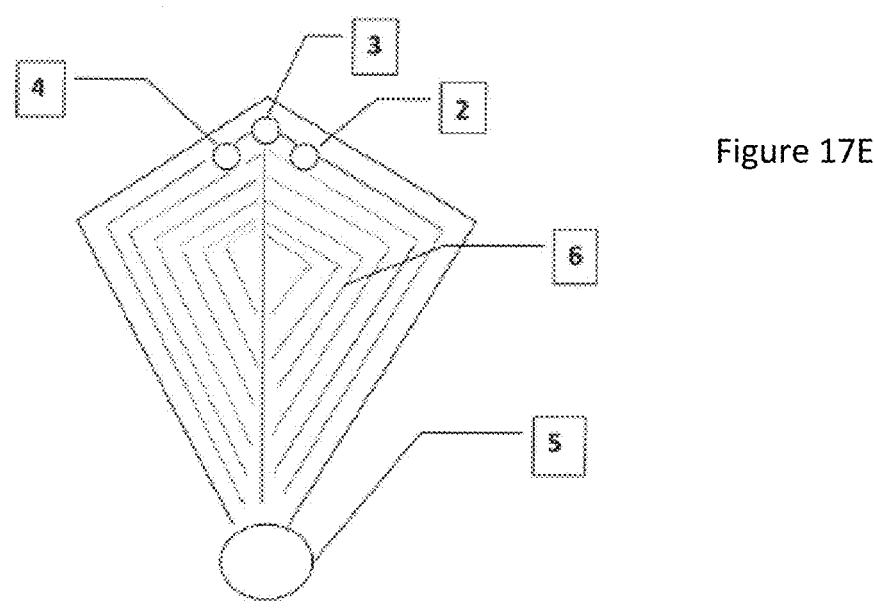
Figure 17E
*Figure 18*
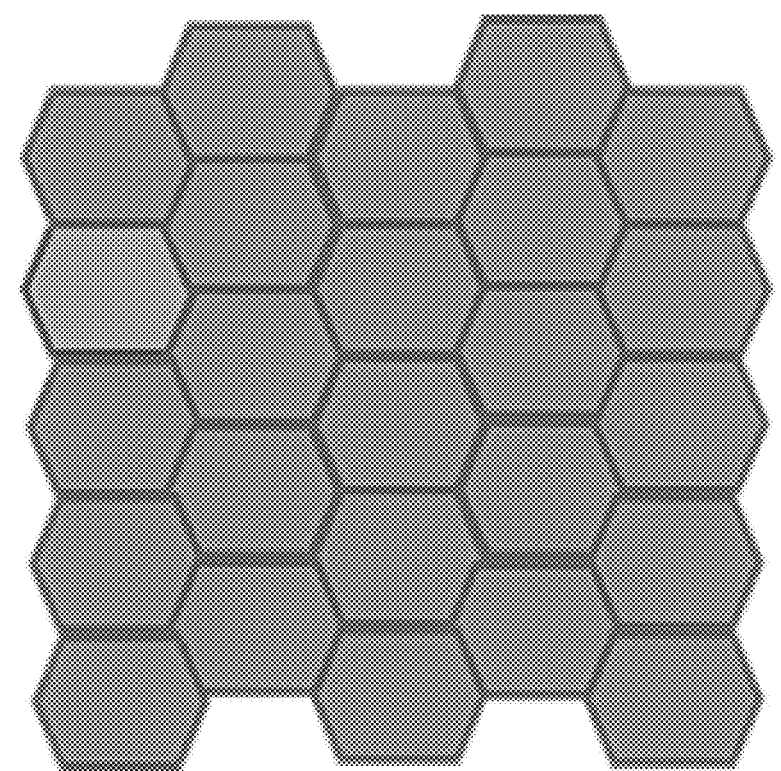

Tissue incubator

| 1 | Medium tank |
|---|---|
| 2 | Lid |
| 3 | Foot |
| 4 | Medium inlet and outlet |
| 5 | Printer table foot |

1       Directional electromagnetic radiation source

2       Non-directional electromagnetic radiation source

3       Piezo printer head

3    Piezo nozzle row
2    Directional electromagnetic radiation source
1    Piezo printer head

METHOD FOR 3D PRINTING OF VASCULARIZED TISSUES AND ORGANS

RELATED APPLICATIONS

This application is a continuation-in-part of International Application No. PCT/EP2020/071804, filed 3 Aug. 2020, which in turn claims priority benefit of EP Application Serial Number 19/189,755.2, filed 2 Aug. 2019, the contents of the aforementioned priority documents are hereby incorporated by reference.

FIELD OF THE INVENTION

The present invention relates to a 3D printing method for producing tissues and organs having vascular structures. The novel, innovative core of this process lies in the following points in particular:

1)

A special capillary ink only reacts in the edge area of the printed drop in the vicinity of drops of other types of ink, so that individual cell layers are created from which the finest capillaries are formed. The non-crosslinked cells inside the drops are washed out and form the inner cavity of the capillaries.

2)

A novel print pattern is disclosed which is characterized by a tissue plane which is made up of various cell types applied in an orderly manner and which is traversed by spatially cut, internally hollow vessels (veins, arteries and capillaries).

The print pattern is characterized by a subdivision of larger tissues or organs into individual modules and a simplification of the print image for an economical printing process. The individual modules, which are printed independently of one another, are glued to superordinate target structures.

3)

Provision of a novel printer table in a medium-filled 3D printing room, which ensures that the printed tissue is supplied with nutrient medium so that the cells do not die.

4)

Provision of controllable printer head supply units that mix the cell and ink concentration per volume unit and the composition of the ink (e.g., from different ink tanks) for the ink droplets according to the specifications of the printing algorithm and that supply the printer heads with the mixed ink.

BACKGROUND OF THE INVENTION

Conventional 3D printing systems do not have the necessary properties to create viable larger tissues and organs due to their specific characteristics and the associated advantages and disadvantages.

In order to produce a larger viable tissue or organ using 3D printing, the nutrition of the printed cells must be guaranteed. Since the cells can only be nourished by diffusion over a distance of approx. 500 μm, a blood vessel system that is also printed is required. The capillary system is located between the arteries and veins, the individual capillary vessels of which have a very small diameter of only approx. 10 μm and are also made up of single-cell layers.

The 3D printing techniques known to date are either methods in which different cell types can be printed simultaneously in one step, but do not achieve the necessary high print resolution (e.g., fused deposition modeling or droplet technologies), or methods, which achieve the required high print resolution, but the selective printing of different cell types within one work step is impossible (e.g., stereolithography printing techniques).

In addition, there are specific 3D printing systems such as Laser Induced Forward Transfer, in which individual cells are removed from a matrix by a laser beam and directed to a collector matrix. Here, a high print resolution can be achieved and different cell types can be printed in one step. However, the printing speed that can be achieved is so low that this technique is only useful for extremely small structures.

Another specific printing system is the further development of 3D stereolithography printing, in which different cell types can also be printed. For this purpose, however, the tissue to be printed has to be changed between reaction tanks with different cell types. This step also allows only very few cell layers and is a relatively slow process with which only smaller structures such as mini-organs can be printed.

Other specific 3D printing processes leave the space for later blood vessels open as a cavity in the printed tissue and initially nourish the surrounding cells with a nutrient medium. To create true capillaries, these tissues must be transformed into an organism that supplies the cavities with endothelial cells and muscle cells surrounding them. This step can also be done later in an incubator. Although capillaries can ultimately be produced in the tissue in this way, the process takes at least days and the natural complexity of the tissue in question is still not achieved. Apart from that, only relatively large vessel diameters can be achieved with these techniques.

Another way to create relatively simple tissues from slowly growing cells such as cartilage or bone is to 3D print scaffolds that are subsequently populated with cells. In these slow-growing tissue types, due to the low turnover of substances, there is enough time for the subsequent formation of capillaries within an organism. However, this procedure is limited to tissue types such as bone and cartilage. For faster growing uncomplicated cell types such as liver cells, it could be shown that very small tissue areas can be successfully transplanted into liver organs. However, these tissue areas can only consist of very small structures, otherwise the cells can no longer be nourished.

All previous attempts to create functional tissues or organs with a 3D printer have resulted in either very small or very slow-growing tissue units, or larger structures that were only viable for a very short time due to the lack of distinct capillaries.

So a 3D printing process is needed that

On the one hand can selectively print different cell types within one work step and which, on the other hand, can achieve the high printing resolution of stereolithography processes.

In addition, the method should have a printing speed with which the printing of whole Organs are really feasible.

In addition, the novel printing system should flush newly formed tissue during the printing process with medium or other liquids suitable for nourishing the cells via the capillaries created in the process.

In particular, the printing process should also provide a new type of pressure pattern, with which it is possible to form a capillary system between arterial and venous structures, in which the liquid (e.g., medium or blood) flowing therein can flow from arterial to venous.

The implementation of the new printing process requires a new type of printer table in essential embodiments, since conventional printer tables of the prior art are not able to supply printed tissue with culture medium during printing.

The implementation of the novel printing process requires a printer head supply unit that mixes the desired cell density and the required ink concentration in the print drop according to the specifications of the printing algorithm.

The object of the invention is achieved by a new type of UV-crosslinking droplet process, which, due to its low-viscosity inks, can use the high-resolution printer heads of photorealistic art prints and which, in addition, increases the print resolution down to a molecular level through highly specific, spatially limited reactions in the edge area of the individual drops.

Previous droplet methods for printing cells are devices in which, similar to an extruder, relatively large droplets of hydrogel inks and cells contained therein are separated from the printer head (thermally or piezoelectrically, see FIG. 1 and FIGS. 2-7). As a rule, there is only one printer nozzle for a cell-type ink. This nozzle has a relatively large diameter, since the viscosity of the hydrogel, which is still in the sol state, is relatively high (FIG. 1 and FIGS. 2-7). The droplets produced in this way are relatively large and usually contain a large number of cells (approx. 2000 cells per droplet).

Surprisingly, it has been shown that by using newly formulated photosensitive cell inks instead of the previously used hydrogels, the viscosity of the cell ink drops could be reduced to such an extent that they can be processed by printer heads from the high-resolution art print sector. That was not possible until now. This means that cell ink drops of a few picoliters (with about 20 cells per drop) can be printed (FIGS. 8-10). With this print resolution it is already possible to print capillaries that are significantly smaller in diameter than the capillaries of previous systems. In addition, it turned out that the print resolution could be further increased by designing the inks in such a way that a crosslinking reaction only took place on the edge area of the capillary ink drops. The remaining volume of the drop, however, does not undergo this cross-linking reaction and is then flushed out or otherwise disposed of in order to subsequently function as a capillary cavity. With this new type of printing process, the print resolution could be increased up to an order of magnitude on a molecular level or individual cells or cell layers and has thus reached the fineness of stereolithography systems. The capillaries that can be printed with this method are as fine as the capillaries of the human organism.

Crosslinking, confined to the edge area of the capillary ink droplets, can occur both from ink components and from a directed laser beam (or other directed electromagnetic source). The reactions that take place can be of a physical, chemical or biological nature (see Examples section).

During the entire printing process, the resulting tissue is preferably flushed with nutrient medium via the capillary structures. For this, a specific pressure pattern is generated during printing, which organizes the formation of capillaries between future arterial and venous structures.

If an entire organ is to be printed and later implanted in an organism or patient, the organ can be connected to the patient's bloodstream for a limited time before implantation in a specially made device outside the body. With this device, the physiological values of the organ can be checked and the optimal time for implantation can be determined.

State of the Art

In Germany, up to 15,000 patients are waiting for a donor organ. A suitable organ can only be found for less than ⅓ of them. For research and pharmacy, around 3 million animal experiments are carried out in Germany every year, which could be made redundant by alternatives. Another area for 3D tissue printing is regenerative medicine, which continues to make great strides [1]-[4].

The 3D bioprint can provide a solution for this and other fields of application. It uses 3D printers to create cellular structures, using additive manufacturing to stack layers of cells to form complex three-dimensional structures. Techniques such as fused deposition modelling, the droplet process and stereolithography are particularly suitable for bioprinting:

Fused Deposition Modeling is an extrusion-based printing process that processes thermoplastics and composites as well as ceramics and metals. It can also be used to print cells in alginate or gelatin gels. The disadvantage of this method is the low print resolution. The droplet process processes polymeric solutions, colloidal suspensions and cell suspensions. Although the resolution of the droplet method is higher than that of fused deposition modeling, it is not sufficient for printing vascular structures. Stereolithography, on the other hand, has the highest resolution that has been achievable to date thanks to the use of a fine laser beam. It processes a viscous photocurable polymer solution, which is exposed to a directed electromagnetic beam to spatially cross-link the solution. Their disadvantage is that only one single cell type can be printed within a reaction tray. If you want to add another cell type, you should preferably change the reaction bath.

The state of the art is inkjet bioprinting of the market leader Organovo, which produces ink droplets each with 10,000 to 30,000 individual cells (source: Organovo). The Organovo company uses bioprinting in particular for the production of liver tissue. As a rule, 3D-printed tissue parts are implanted in the damaged organ, which support the existing liver in their mode of action and thus extend the life of this organ until a suitable donor is found.

In extrusion bioprinting, bioinks are ejected from a small needle using mechanical pressure. In this way, the entire cell structure is printed layer by layer. This method is used, for example, by bioprinters from Envisiontec GmbH . The working speed is relatively high, but unfortunately the print resolution is very low.

Cellbricks and TissUse ("organ on a chip"), for example, use stereolithography. It provides the highest print resolution because a hydrogel is crosslinked with the help of a laser beam. However, only one cell type can be printed with this method. In order to assemble the tissue from several cell types, the resulting tissue preferably has to be changed through different reaction tanks, which slows down the process and the printed tissue only reaches small dimensions.

In addition to these most commonly used methods, there are a number of methods that have emerged from modifications:

Some techniques aim for the very fine capillaries (as small as 10 μm in diameter) to form between the larger printed veins and arteries during the cell culture itself [5]. The problem here is that the printed tissue has to be matured for a long time. The longer the tissue is kept in cell culture, the greater the likelihood of artifacts.

Another approach is the printing of tubular structures with a polymer, which is then depolymerized again and flushed out, thereby releasing a cavity for the formation of a vascular system [6], [7]. However, this approach is insufficient and differs from the novel method disclosed here in two respects: 1) it is a tube without endothelial cells and the finest ramifications, a longer incubation (with artefacts to be expected) is required and 2) the pressure resolution is far too high low to be able to create a true capillary system.

Another solution is tandem printing: first, the vascular network is printed using a stereolithography system (which has a high resolution but can only print a single cell type). Then the printed vascular structure is transferred to another 3D printing system (which does not have good resolution but can print different cell types) where the remaining tissue cells are printed [5]. In particular, the printed vascular structure must be removed from the reaction container of one 3D printing system and transferred to the reaction container of the other 3D printing system. Particular differences to the method disclosed here are: 1) No single cell layers can be printed, the structures would be too fragile if changed and 2) two different printers are required, the risk of contamination increases if changed.

SUMMARY OF THE INVENTION

In order to be able to implement the method disclosed here, a printer table is required in preferred embodiments, which can supply the printed tissue with nutrient medium so that the cells are not undersupplied or die off. In addition, the printer table must preferably be located in a liquid-filled pressure chamber.

Printer tables and print rooms for conventional 3D printing processes cannot be used for this. For example, most 3D printing systems (e.g. FDN, SLS, BJ and others) have a dry print table in a dry print room and have no means of liquid intake.

A few 3D printer types have a liquid-filled pressure chamber (e.g. SLA), but there is no supply system for the printed tissue with an additional liquid inlet and outlet, as is required for 3D printing of tissues and organs with vascular structures.

The novel printing system disclosed here is based on a droplet process and differs from previous droplet systems in several aspects, which are listed below:

1)

Novel photosensitive bio-inks are used, which are so low-viscosity that they do not clog the fine printer heads of photorealistic art prints. Previous ink drops contain about 2000-3000 cells and consist of hydrogels (Organovo). The hydrogel components are the reason for the relatively large drops, since their viscosity is relatively high even in the sol state. The droplets produced in the process disclosed herein are very small, low viscosity and contain about 20 cells or less. The printed cell mass is achieved by the fact that the art print printer heads have around 160 nozzles or more instead of just one nozzle per ink type (as was previously the case).

At the same time, the inks have a formulation that makes it possible to crosslink immediately and thus prevent the drops from running. Previously existing hydrogels in the droplet process, which were photosensitive, used curing, which was triggered by a light source outside the printer head and lasted over a longer period of several minutes. In the novel method disclosed here, the source of the electromagnetic waves (e.g. visible light, IR, UV) is located directly in the printer head and can be both fixed and directional.

2)

Special bio-inks (capillary inks) within the novel printing system disclosed here crosslink only selectively to a limited extent in the edge areas of the drops or in the areas adjacent to the drops of other inks. This selective crosslinking can be triggered either by components of the ink or by directed electromagnetic radiation. The crosslinking can be biological, chemical or physical. The components of the drops of the special bio-inks that are not in the edge area are rinsed out or otherwise removed, creating the necessary cavity for the capillaries that are created.

Non-crosslinked capillary cells (eg endothelial cells) that are flushed out into the surrounding tissue become, for example, the starting point for later new capillary structures or are lost during tissue differentiation.

This process makes it possible to obtain a print resolution in which only individual molecules or individual cells are specifically crosslinked. So far, only high-resolution stereolithography processes have had the ability to network individual cells. The droplet sizes are preferably between one femtoliter and 10 microliters.

The printed image produced in this way has a new, previously unattainable quality On the one hand, different types of ink (e.g., muscle cells, nerve cells, structure inks, capillary inks) can be printed in a photorealistic manner at the same time and in which on the other hand, due to the selectively limited edge cross-linking of the capillary inks, the print resolution is so high that individual cell layers (e.g., endothelial cells) are formed.

3)

Due to the formation of a resilient blood vessel system during the printing process, it is possible to supply the tissue or organ being created with sufficient nutrients even during the printing process. The connections to the pump systems required for this are initially provided by the printer table and the pressure plate (FIGS. 2-7) located on it. In order to create even finer connections for vessels and capillaries that are individual for each tissue structure, individual connections are printed from these connections. In preferred embodiments, either capillary and tissue inks or initially a structured ink can be used.

If a structure ink is used, the transition between structure ink and cell ink can take place via a gradient, which stabilizes the system. So far there is no droplet technology in which such a supply system for printed cells exists.

After the print has been completed, the removable print foil (on which the finished print is located and has the inlet and outlet connections for liquids) can be further cultivated in an incubator (FIG. 19).

4)

A novel complex pressure pattern is disclosed which enables the formation of capillaries between arterial and venous structures in which the liquid (eg medium or blood) flowing therein flows from the arterial region into the venous region. So far, such print patterns are not known and could not be implemented due to the deficiencies of the current state of the art.

The print pattern is unique because different cell types can be printed in a single printing process and at the same time ordered structures can be created that are only a few molecules in size.

This print pattern is preferably characterized by the following properties:

Specific algorithm for calculating the print image in relation to the type of cells used (type of ink), as well as in relation to the distance and size of the capillaries and the arterial and venous structures. The algorithm is based on the one hand on the requirements for an optimal capillary supply of the module to be printed and on the other hand on the physiological and anatomical requirements of the respective tissue structure.

The tissue/organ consisting of different tissue types and vessels is divided into individual modules, which in turn are divided into pressure levels (slices). The different cell types printed on a print plane in the module correspond to their vascular or tissue position within the respective tissue or organ.

A comprehensive capillary system with a capillary inner diameter of 5 micrometers and larger is preferably produced. The capillaries preferably have a distance of about 50 micrometers from each other on each individual printing plane. The liquid flowing in it flows from arterial to venous after the pressure has been completed.

The sum of the individual pressure levels leads to a single module. The module preferably has an ascending and a descending vessel (FIGS. 15 and 16), both of which are connected to one another by intervening fan-shaped smaller capillaries. The ascending and descending vessels become the connections for arterial supply and venous drainage. The resulting microcirculation represents the smallest supply unit in the printed tissue.

Basic modules are assembled and glued to form larger tissues or organs. The ascending and descending vessels from the micro-circulations are combined to form the main supplying and draining vessels.

5)

Provision of a novel printer table which can move in the Z-direction of a medium-filled print space and which has supply connections through which the printed tissue is controllably supplied with medium.

6)

Provision of a printer head supply unit in which the cell density and the ink concentration are controllably mixed. The mixed ink for the printer heads is composed according to the specifications of the printer algorithm. In principle, there are tissue inks, capillary inks and structured inks in the process, although other ink types can also occur.

BRIEF DESCRIPTION OF THE DRAWINGS

FIG. 1: Exemplary schematic printer structure and function;

FIGS. 2-7: Exemplary structure of the printer table and how it works;

FIG. 13 are selective factors-cleavable protecting groups for thiol groups at the wavelengths of 325 nm, 400 nm and 436 nm (source: wavelength-selective cleavable photolabile protecting groups for thiols, [4]);

FIG. 16: Flushing of the resulting capillaries with medium ascending direction (left) and descending direction (right);

FIGS. 17A-17E: Liver-organ module;

FIG. 18 Superimposition of individual printed liver-organ modules;

DETAILS OF THE INVENTION

Figure 2:
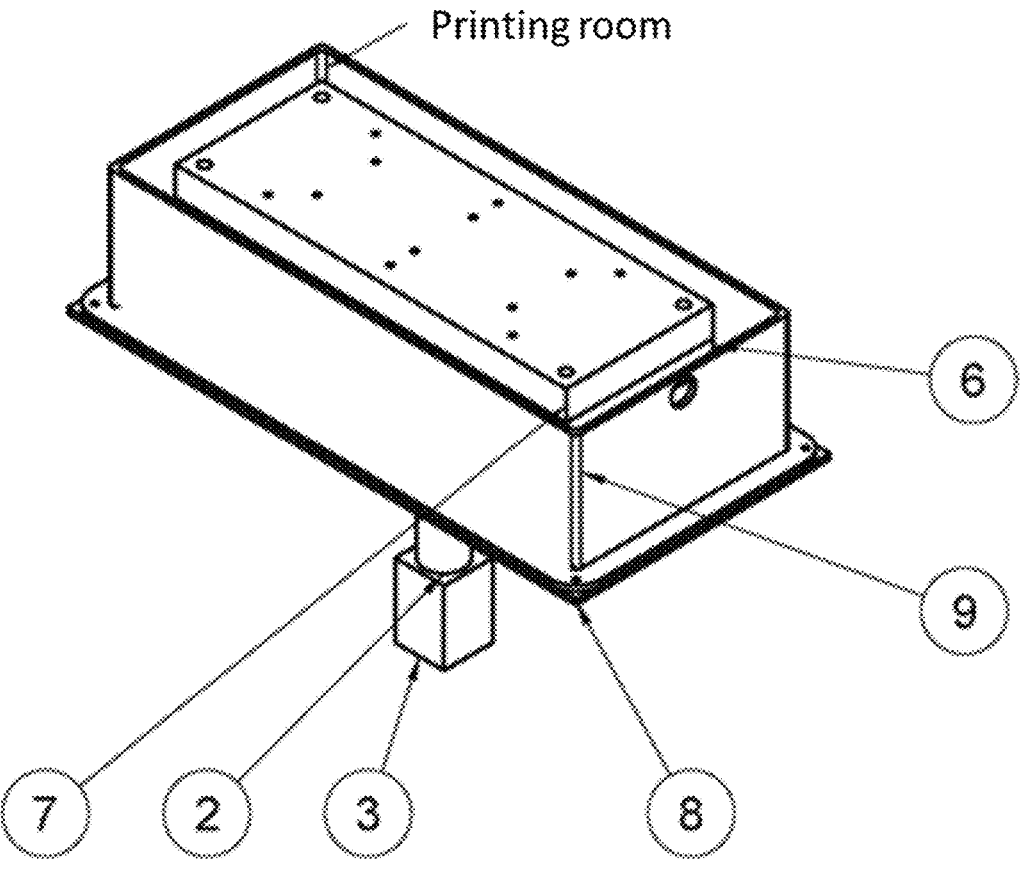

It requires a 3D printing process that can selectively print different cell types within one work step and that the high print resolution achieved by stereolithography processes.

In addition, the method should have a printing speed with which the printing of whole organs are really feasible.

In addition, the novel printing system should preferably flush newly formed tissue with medium or other liquids suitable for nourishing the cells via the capillaries created during printing (FIG. 16).

The printing process should preferably also provide a new type of pressure pattern, with which it is possible to form a capillary system between arterial and venous structures, in which the liquid (e.g., medium or blood) flowing therein can flow from arterial to venous.

In particular, the printing system should have a device that ensures a sufficiently high cell concentration per unit volume in the ink drop without the cells clumping together in the printer head.

The preferred sequences of the procedure are:

providing at least one capillary ink and another bio-ink with cells and crosslinking molecules in a droplet printer;

applying at least one drop of the capillary ink and the bio-ink to a reaction plane;

bringing electromagnetic waves into contact with the crosslinking molecules in these droplets at the reaction level;

and activation of the crosslinking molecules by means of non-directional or directed movements of the electromagnetic waves in the droplets, as a result of which crosslinked structures are formed and vascular structures are thus obtained.

Providing at least one capillary ink that crosslinks only in the edge area of the drop at the border to drops of other inks Rinse or eliminate the non-crosslinked droplet components of the capillary ink Providing low-viscosity, electromagnetic wave crosslinkable bio-inks that can be processed by the high-resolution print heads of photorealistic printers and that crosslink immediately after exposure to the electromagnetic waves Provision of a supply system for the printed cells in the printer with nutrient medium (provision by the printer table); other preferred processes are:

Provision of a printer head supply unit, which preferably regulates the cell density and the ink concentration in the ink drop according to the specifications of the printing algorithm and guides the mixed inks into the printer head.

Provision of a novel printer table in a medium-filled 3D printing room, which ensures that the printed tissue is supplied with nutrient medium so that the cells do not die Providing a specific algorithm for calculating the print image in relation to the type of cells used (type of ink), as well as in relation to the distance and size of the capillaries and the arterial and venous structures. The algorithm is based on the one hand on the requirements for an optimal capillary supply of the module to be printed and on the other hand on the physiological and anatomical requirements of the respective tissue structure.

The sum of the individual pressure levels preferably leads to a single module. The module has at least one ascending and one descending vessel connected by fan-shaped capillaries. The ascending and descending vessels become the connections for arterial supply and venous drainage. The resulting microcirculation represents the smallest supply unit in the printed tissue.

Individual modules are assembled and glued to form larger target structures, the supplying and draining vessels are combined to form common connection vessels.

The 3D printing method according to the invention is implemented using a high-resolution droplet printer and a device for applying electromagnetic waves, preferably a laser, a UV lamp or a diode. The inks used are low-viscosity inks that can be processed by the high-resolution printer heads of photorealistic art prints and that crosslink directly under the influence of electromagnetic waves, preferably within a second. The ink drops can have volumes from 1 femtoliter to 10 microliters.

The 3D printing method according to the invention also includes at least one capillary ink that selectively crosslinks in the edge areas of the drops or in the areas adjacent to the drops of other inks. This selective cross-linking is either caused by ink components (of the capillary ink and/or the adjacent bio-inks) or by directed electromagnetic waves that cross-link individual cells in the edge area of the capillary ink drops. The non-crosslinked areas of the capillary inks are flushed out or otherwise eliminated and form the cavity for the capillary and vasculature.

Due to the crosslinking that is spatially limited to the edge area of the capillary ink drops, not only individual cells, but even individual molecules can be activated to form a cross-linking reaction or other layer formation. The print resolution achieved through this process is even higher than that of stereolithography processes, which is around 20 nm.

Exemplary reactions in the edge area of the capillary ink drops can be:

Thiol-ene reactions (also alkene hydrothiolation)

Key and lock reactions

Nucleophilic ring openings

Self-assembly of molecules and particles

Selective factors on the cells of the capillary inks and/or bioinks

Radical or cationic polymerization reactions

Antibody reactions

Reactions with click chemistry components (e.g., cycloaddition, others)

other processes in which it is possible for two adjacent peripheral areas to carry out a spatially limited reaction or interaction with one another or in which a "self-assembling" process occurs.

Figure 8:
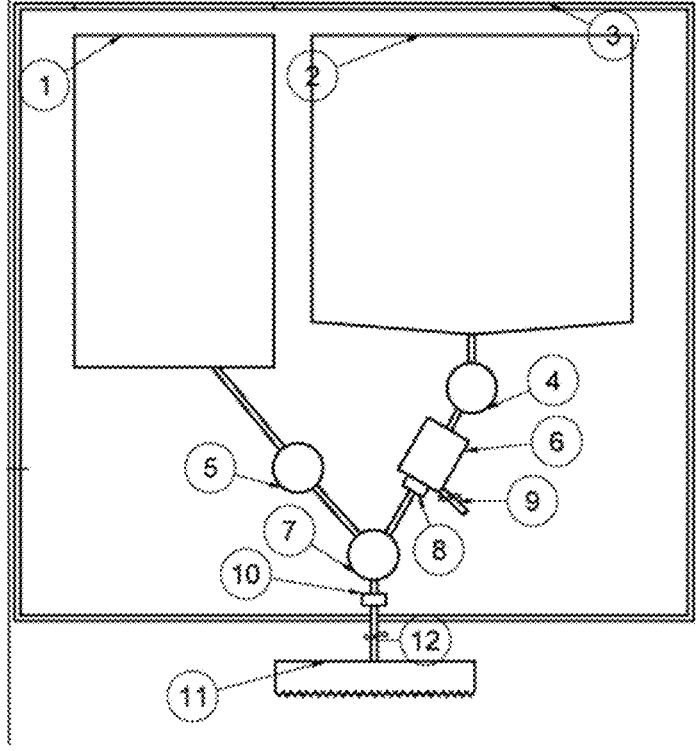
FIG. 8: Exemplary structure of the printer head supply unit and how it works.

Since the ink components in the ink drop required for the respective tissue print can vary in terms of cell density and ink concentration and are determined by the printing algorithm, it was an object or aspect of the invention to provide a printer head supply unit upstream of the printer head (FIG. 8). In this, the cultivated cells are pumped from the cell tank into a cell concentrator by a pump. Here the cell density is concentrated and excess medium is separated. A defined cell concentration is forwarded to a mixing unit via a cell counter. A certain volume is also introduced into this mixing unit from a tank for ink concentrate. The mixing unit mixes the inks according to the specifications of the printing algorithm for the required tissue type and sends them to the printer heads. The number of printer head supply units depends on the number of inks required and can vary. However, the inks can also be mixed without specifying the printing algorithm.

In order to keep the printed tissue alive, it may be necessary, for example, to connect it to a supply circuit during the printing process. In addition, the printed tissue must preferably be in a medium-filled print space during printing so that it does not dry out. Conventional printer tables do not have such a supply system. An object or an aspect of the invention was therefore to provide a printer table that supplies the tissue with nutrient medium during printing through medium inlet and outlet (FIGS. 2-7).

The liquid for the medium inlet and outlet is fed to the printer from outside, for example, by means of an adjustable pump system. The running direction of the pumps can be reversed. The supply takes place in particular via a hose system, which is connected to the printer table base via connections (e.g., Luer). The medium is guided through the printer table into the printing plate via the spigots of the printer table foot. There is an exchangeable silicone membrane between the printer table base and the pressure plate, which separates the pressure chamber filled with medium from the base plate and seals it against the medium (FIGS. 2-7). The silicone membrane is necessary for the seal, since the base plate of the pressure chamber is penetrated by the pin of the micrometer screw and allows the printer table to move up and down.

Experience has shown that conventional sealing systems such as mechanical seals are potential sources of contamination. The innovative solution to the problem with a removable silicone membrane has the advantage that it is easy to clean and sterilize. Plus, they're cheap to replace. Due to its high elasticity, the printer table setting can be freely selected. The silicone membrane also acts as a seal between the base plate and the pressure chamber wall.

In order to be able to change the printing table (within the printing space) without any problems, the printing table foot (outside the printing space) has a magnet that attracts the printing table. The connecting pins of the printer table base are also pressed and sealed by the magnetic force in the seal of the counterbore of the printing plate. This preferred solution according to the invention leads to extremely simple handling when changing the printing table.

The tissue to be printed should be penetrated by many vessels in order to be able to adequately supply it (FIG. 15). In order to be able to provide the required print pattern, a specific algorithm is required in relation to the cell type used (ink type) and in relation to the distance and size of the capillaries and the arterial and venous structures. The algorithm is based in particular on the one hand on the requirements for an optimal capillary supply of the module to be printed and on the other hand on the physiological and anatomical requirements of the respective tissue structure. The tissue/organ consisting of different tissue types and vessels is subdivided in particular into individual modules, which in turn are subdivided into pressure levels (slices). The different cell types printed on a print plane in the module correspond to their vascular or tissue position within the respective tissue or organ. In particular, a comprehensive capillary system with a capillary inner diameter of approx. 10 micrometers and larger is produced. The capillaries preferably have a distance of about 50 micrometers from each other on each individual printing level. The liquid flowing in it flows from arterial to venous after the pressure is completed (Fig.

The sum of the individual pressure levels leads to a single module. The module preferably has an ascending and a descending vessel, both of which are connected to one another by intermediate, fan-shaped, smaller capillaries. The ascending and descending vessels become the connections for arterial supply and venous drainage. The resulting micro-circulation represents the smallest supply unit in the printed tissue. Individual modules are assembled and glued to form larger target structures.

The connection openings required for the vascular system, onto which the vessels are printed, are located on a printing plate which is fastened to the printing table (FIGS. 2-7). The function of this pressure plate is to distribute the medium from the two main connections of the pressure table to the individually required secondary connections. Since each tissue has an anatomical structure, the plate should be created individually for each printing process. Each printing plate is made in advance using a 3D print (e.g. FDM, SLS, BJ, others). The files for printing also come from the system algorithm for organizing the printer. The printing plate corresponds to an individually created tool for printing and is preferably made of a polymer.

A pressure foil, preferably made of biodegradable or resorbable polymer, is applied above the pressure plate and has the same connections as the pressure plate. The printing foil is used for easy and non-destructive detachment of the tissue from the printing plate. Due to the biodegradability of the polymer, the printing film is degraded in the body in a short time (FIGS. 2-7).

Figure 19:
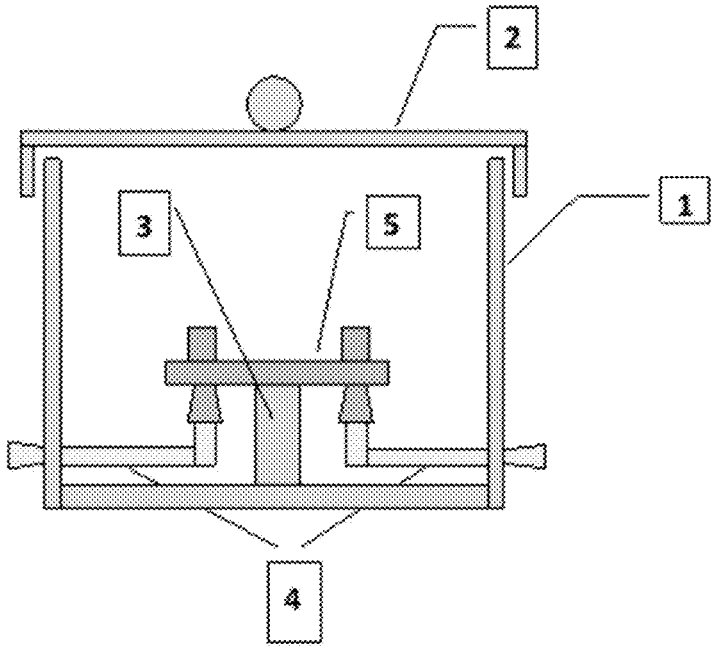
FIG. 19: Exemplary structure of an incubator.

In order to allow the printed tissue to mature without any problems in a commercially available incubator, the printing table with the printing plate (optionally only the printing plate) is transferred to an incubator vessel (FIG. 19), which is stored in the incubator. This incubator vessel consists in particular of a medium-filled tub with a lid to be placed on. A base is permanently installed on the bottom of the tub, on which a printer table base of the same construction is exchangeably attached. The supply and discharge medium hoses to the printer table base are routed through openings in the incubator vessel. The printer table including the printing plate, printing film and printed tissue is placed on the pins of the printer table base (without the silicone membrane) using magnetic force (FIG. 19).

Other Embodiments

In a preferred embodiment of the invention, the droplet size is between one femtoliter and microliters. Advantageously, this droplet size allows the inventive task to be solved surprisingly well in a thiol-ene reaction. Thiol-modified molecules inside the drop do not crosslink under these conditions and are flushed out.

In another preferred embodiment, the capillary inks have thiol-modified molecules, the surrounding bioinks have allyl-modified molecules, and a photoinitiator to initiate the crosslinking reaction. This cross-linking reaction takes place within the bio-inks between the allyl-modified molecules. The thiol-modified molecules of the capillary inks cross-link only selectively in the edge area with the allyl-modified molecules of the bio-inks.

In another preferred embodiment, a copper(I)-catalyzed 1,3-dipolar cycloaddition of azides and alkynes leads to a cross-linking reaction in the edge area of the capillary inks, with azide-modified and alkyne-modified molecules only meeting in the boundary area of the capillary ink droplets to form bioinks.

In a further preferred embodiment, the capillary ink contains epoxide group-modified molecules which can cause nucleophilic ring opening with OH groups or $NH_2$ groups of molecules from the bioinks or which undergo acid-catalyzed or base-catalyzed ring opening by components from the bioinks.

In another preferred embodiment, capillary inks and bioinks contain molecules that form self-assembling structures in the size range, for example via ions, aptamers or other structures that tend to self-assembling.

In a further preferred embodiment of the invention, it is provided that the cells contain a selective factor by which they are selectively crosslinked within a droplet by means of directed movement of the electromagnetic waves.

The new low-viscosity bioinks and capillary inks that can be crosslinked by electromagnetic waves are made up of a) the respective cell type (optionally with a factor that is selective for the cell type) and crosslinking molecules.). In addition, growth factors, signal molecules, particles for the development of an impulse conduction or other molecules can also be components of the ink.

Figure 14:
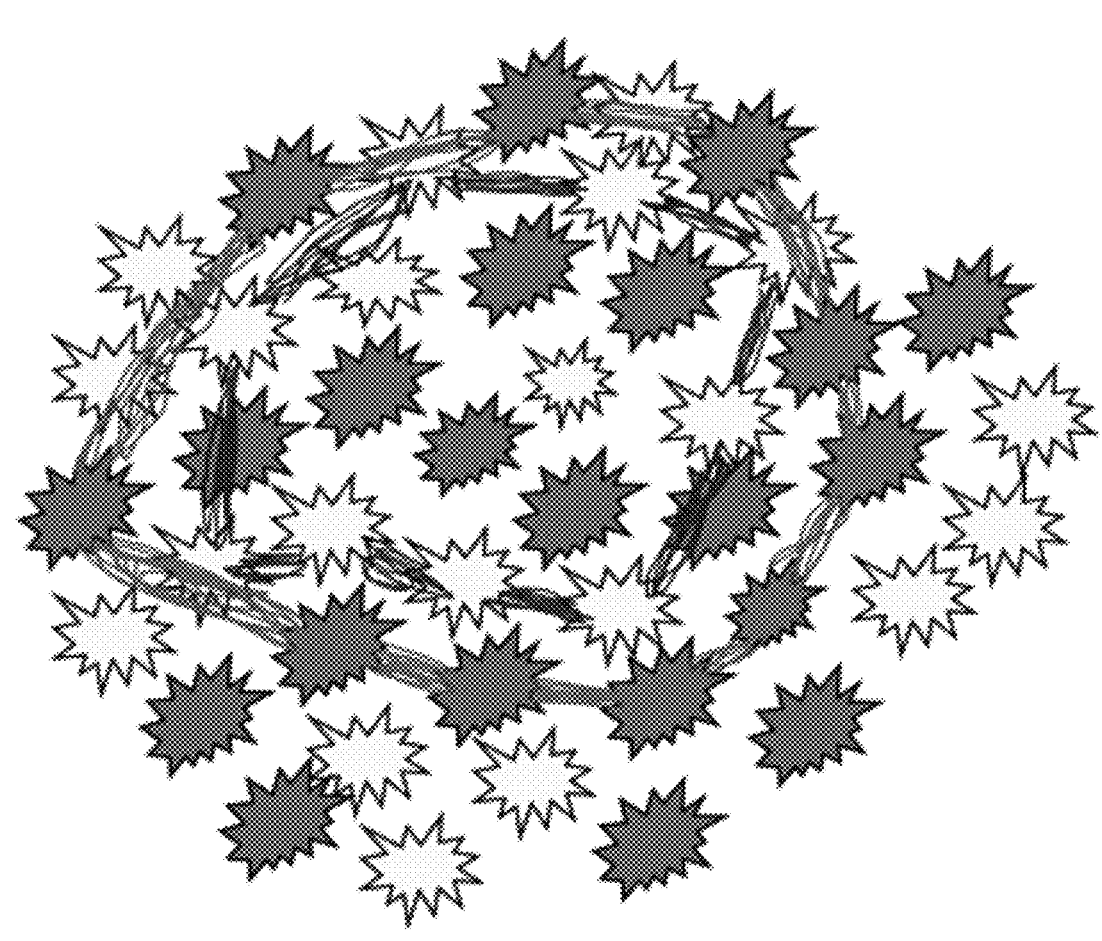
FIG. 14 are cells with selective factor. Light cells show endothelial cells, dark cells show muscle cells. Both cell types are present as a mixture in a capillary ink drop and can be selectively activated by 2 laser beams with different wavelengths for the cross-linking reaction.

A selectively acting energy source can trigger a cross-linking or polymerisation reaction from a droplet containing a mixture of different cells, in which only the intended cell type is hit. Preferably, the non-crosslinked cells can be removed. For example, a small droplet as small as 5 picoliters (about 20-200 cells) may consist of a mixture of vascular endothelial cells and myoblasts. In a preferred embodiment, the ring of a fine capillary is then formed from this mixture using a nanometer-precise laser beam. By means of a specific input of energy from a laser 1, only the endothelial cells that are located along the inside of the ring are preferably crosslinked in the mixture. With a different specific energy input from a laser 2, only the adjacent myoblasts on the outer side of the ring are crosslinked in this preferred embodiment (FIGS. 13 and 14)

In a further preferred embodiment it is provided that the non-crosslinked cells inside the vascular structure are removed by means of a laser.

Bioinks consisting of a particularly homogeneous cell type are also preferably crosslinked in order to print larger homogeneous tissue areas, for example.

In a preferred embodiment, the cells to be networked are included in a network that is being formed.

In a further embodiment, the cells themselves are net-worked with one another or with a network. To do this, they have a crosslinking molecule that is anchored in the cell membrane.

Due to the comparatively fast printing process, it is surprisingly possible to transfer the printed tissue relatively promptly to an incubator in which further maturation is triggered by environmental factors (eg chemical, molecular-biological, or flow stress).

Other crosslinkable inks are preferably printed at specific positions that carry support functions for the tissue, carry factors that are important for the physiology of the cell, or carry growth factors, markers, signaling molecules, receptors or other binding sites (key-lock principle).

Similar to the inkjet printer for photorealistic art prints, the printer head preferably has a larger number of nozzles that are adapted to the respective rheology of the ink. The printer also preferably has one or more sources of omnidirectional or directional electromagnetic waves, which initiate the crosslinking reactions.

In a preferred embodiment, a printer head for photorealistic art prints is used, which has been additionally modified with one or more sources for electromagnetic waves.

In a further embodiment, a printer head composed of modules is used, each module corresponding to a photorealistic art print head with one or more electromagnetic wave sources.

In a further aspect of the invention, this relates to a novel construction of a printer head (see FIG. 9 to FIG. 12) and a novel printing process in which different energy sources are selectively used to trigger different reactions (FIGS. 9-12).

FIG. 13 and FIG. 14 show schematically how certain cells can be cross-linked with each other via various photoinitiators with the help of light of a specific wavelength. Lasers, diodes or other energy sources can be used as the energy source (see Examples section).

In a preferred embodiment, the printed tissue is fed during the printing process. The connections for the culture medium on the base plate are individually extended to the tissue to be printed using structured inks. Starting from the connections on the bottom plate, finer connections with smaller diameters are printed with a texture ink.

In a further embodiment, the printer head is equipped with bubble technology, piezo technology or other printer head technologies.

The source of electromagnetic waves, in one embodiment, is a non-directional source, such as a diode, laser, UV lamp, or other source.

In a further embodiment, the source for electromagnetic waves is a lens that can be swiveled through 180°. The energy source is controllable and movable, allowing the laser beam to form any pre-programmed shape. In a further embodiment, the light is generated in an external light source and transported to the point of exit via fiber optic cables.

In one embodiment, the wavelength of the electromagnetic waves is in the UV, visible, or IR spectrum.

In a preferred embodiment, a suction device or compressed air device is provided to remove the flushed non-crosslinked ink material.

Figure 11:
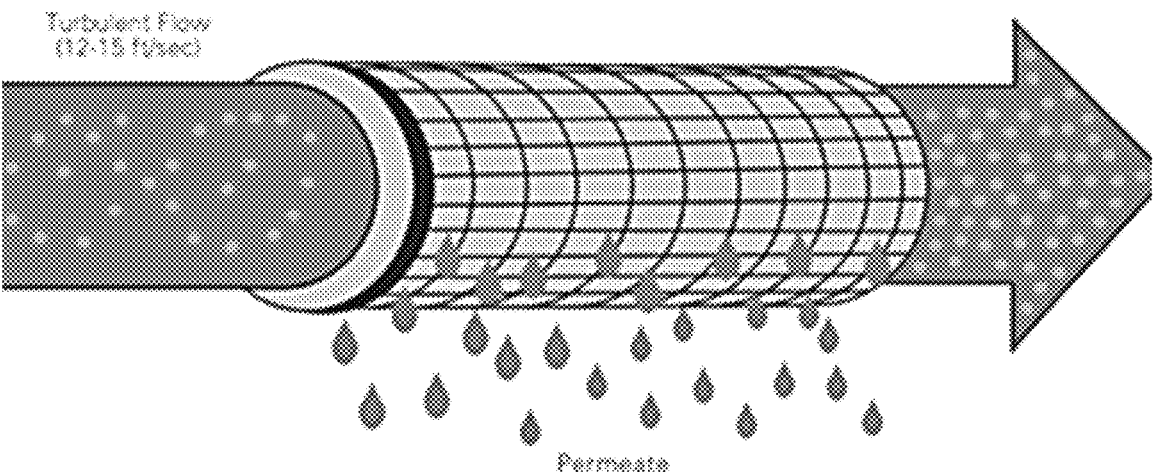
FIGS. 11 and 12: Preferred designs of the cell concentrator (6) for concentrating the cells through dynamic filtration.
Figure 12:
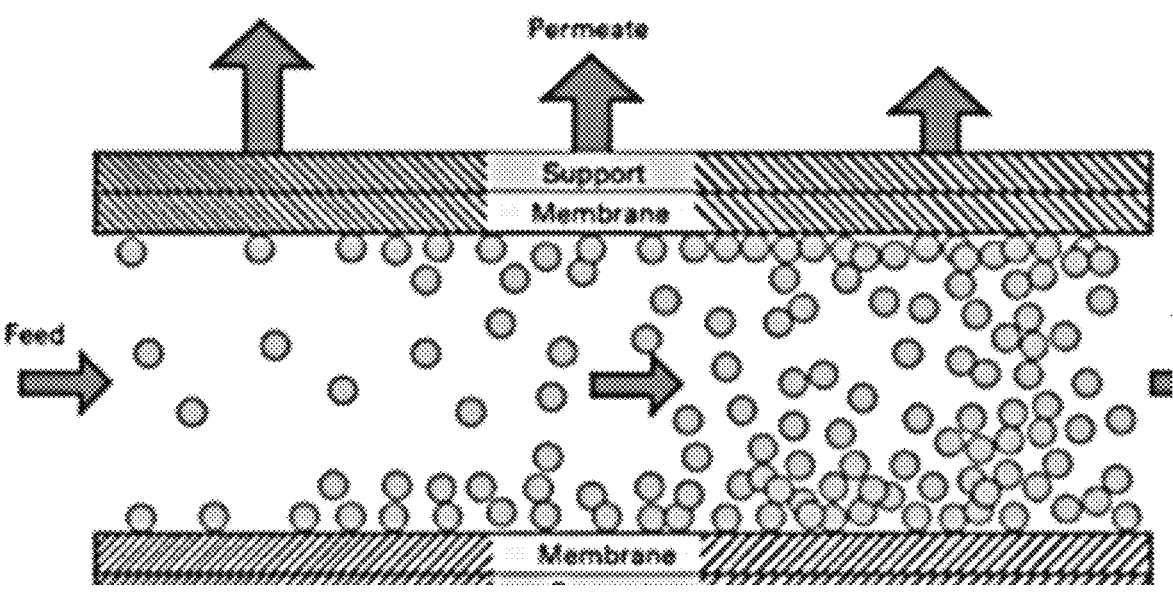

In one embodiment, the vacuum is controllable and only activated when the suction device is lowered. The distance between the suction device and the object to be printed is controlled by a laser (FIG. 11 and FIG. 12).

In a further embodiment, no additional device is required to remove the ink or cell material that has been flushed out, because the flushed out cells form starting points for new capillaries in the surrounding tissues or are incorporated or perish during the differentiation of the surrounding tissue.

In another embodiment, the non-crosslinked ink material is destroyed by a directed laser beam.

In a further embodiment, the non-crosslinked cells, cell debris or ink are flushed out by a device and escape into the reaction space.

In one embodiment, a gas atmosphere is generated above the pressure level via gassing nozzles (e.g. inert gas, $CO2$, etc.)

In one embodiment, the wavelength and beam width of the electromagnetic wave source is modulatable. The printer has one or more modulatable sources for the targeted electromagnetic radiation.

In a further embodiment, a femtosecond laser is preferably used.

In one embodiment, the gas content (eg $CO_2/O_2$), the pH value and other important cell culture parameters are regulated during the printing via the nutrient medium. In addition, the gas exchange is also regulated via the gas content in the reaction space.

In one embodiment, the method is performed bottom up or up to bottom.

In one embodiment, the reaction vessel of the printer is optionally inserted into the printer as a disposable insert and can be removed after printing. After printing, the tissue or organ is in a state where it can be brought into contact with the patient or transferred to cell culture. The reaction vessel has connections for the inflow and outflow of nutrient medium or blood to nourish the tissue.

In one embodiment, the reaction vessel is cooled.

In one application form in the patient, the reaction vessel is connected to the patient's bloodstream outside the body. Further maturation occurs as a result of the patient-typical growth and differentiation factors provided, as well as the blood pressure within the still-differentiating vascular system. During this phase, samples are optionally taken from the system in order to monitor the degree of maturity (degree of differentiation) of the tissue or organ and to determine the optimal time for implantation. The reaction vessel has additional connections for taking these samples.

In connection with the method according to the invention, it is advantageous if certain cell types are specifically hybridized with molecules before the 3D printing in order to make the cells in a mixture selectively addressable. The connection consists of a selective factor and an anchor molecule. The selective factor should preferentially trigger the cross-linking. The anchor molecule is preferably used for docking to the cell membrane. The selective factor can also bind directly to the cell surface without an anchor molecule if its chemical and physical properties allow it. A spatially controlled energy beam from electromagnetic waves, specially directed in its wavelength and frequency, hits a selective factor of a specific cell type and activates it, for example, by splitting off a protective group, activating a photoinitiator, activating a reaction partner or activating a lock and key -Component. Other cell types are unaffected by this crosslinking reaction. (FIGS. 13 and 14, see Examples section).

In one embodiment, the selective factor has a lipophilic molecule, for example perfluorocarbons or lipids, as anchor molecule. In another embodiment, the selective factor has cationic molecule areas or molecule areas with positive partial charges as anchor molecule. In a further embodiment, the selective factor has peptide compounds as anchor molecule, for example cell-penetrating peptides or polynucleotides.

In connection with the teaching according to the invention, novel bio-inks are used:

In contrast to the previously used higher-viscosity bio-inks of conventional droplet processes with the long-chain macromolecules contained therein, the novel bio-inks of the process disclosed here are very low-viscosity and contain photoinitiators. They contain very short-chain smaller crosslinking molecules that crosslink immediately after exposure to electromagnetic waves. In the preferred embodiment, these molecules have allyl modifications or thiol modifications.

In a further embodiment, the pressure chamber is gassed.

In a further embodiment, the capillaries are not printed at an angle of 10-90 degrees to the printing plate but parallel (0-10 degrees) to it.

In a further embodiment, the capillaries are rinsed before the ring closure.

General Process of Printing—Theoretical Basics and Preferred Versions

The invention disclosed here describes a method for 3D printing of organs and tissues. Larger print areas are broken down into individual modules, printed independently of one another (on the same or on different printers) and then assembled and glued to the target organ or tissue (eg with fibrin glue). Inflowing and outflowing vessels of the individual modules are combined to form inflowing or outflowing main vessels. The individual module is preferably a cubic structure with a defined edge length.

A tissue or an organ may have the same structure, but they are not identical. Each individual, even within the same species, differs slightly from another. This is not only reflected in the size, but also in the individual development. The muscles of an athlete, for example, are much more capillarized than those of a non-athlete due to the higher oxygen requirement. The body adapts to the environmental conditions and is therefore never identical and experiences a constant build-up and breakdown.

It is therefore the function of the tissue that is decisive and not the exact anatomical reproduction of the patient's tissue. Therefore, a modular system is disclosed here, which enables the function of the tissue but has also been simplified and systematized to the extent that the 3D printing of the tissue can be carried out economically.

The basic building block of the tissue or organ is the cubic individual module (1) (FIGS. 15-18) with a defined side length. To supply the tissue, which can consist of one or more cell types and can therefore also form a functional tissue such as an organ, it is supplied on one side by an ascending vessel (2), which later forms the artery. The descending vessel (3) on the opposite side forms the vein. Smaller vessels (4) fan out from each of the vessels, which extend to the level of the opposite vessel on the other side and run parallel to one another (FIG. 2). The smaller vessels (4) are connected to one another by bridging vessels (6), which later form the capillaries and close the "blood circuit" and form a microcirculation (FIGS. 15-18).

The microcirculation (FIG. 15) represents the smallest supply unit in the printed tissue. Here, the medium is conducted via the ascending vessel (artery) (2) into a small vessel (4), which belongs to the ascending branch. The medium flows from the smaller vessel via the bridge vessels (6) into a smaller vessel (4) below, which belongs to the descending branch and flows into the descending vessel (3).

Since when printing the vessels with capillary ink, many cells are printed per drop and only the cells on the edge areas are able to network with the surrounding tissue, the excess cells have to be rinsed out. For this purpose and to supply the printed cells, after each completion of a micro circuit, it is flushed with medium for a short time. With each rinsing process, the micro circuits below the last micro circuit are also rinsed and the cells supplied. The flow of medium flushes out the uncrosslinked cells. Horizontally running vessels are not optimal for this, which is why the printed vessels all run at an angle of 10 to 90 degrees to the printing plate.

The ascending and descending vessels (FIGS. 15, 16) (2 and 3), rise at an angle of 90°. The vascular compartments (5) can rise at an angle of 10-90°. Printing is ascending up to the middle of the individual module, then descending, so that the smaller vessels always run ascending to the printer plate. In this way, the excess cells can be rinsed out easily from the unfinished printed vessels. If a micro circuit (7) is closed, the medium can run off via the descending vessel (FIGS. 15 and 16).

Figure 5:
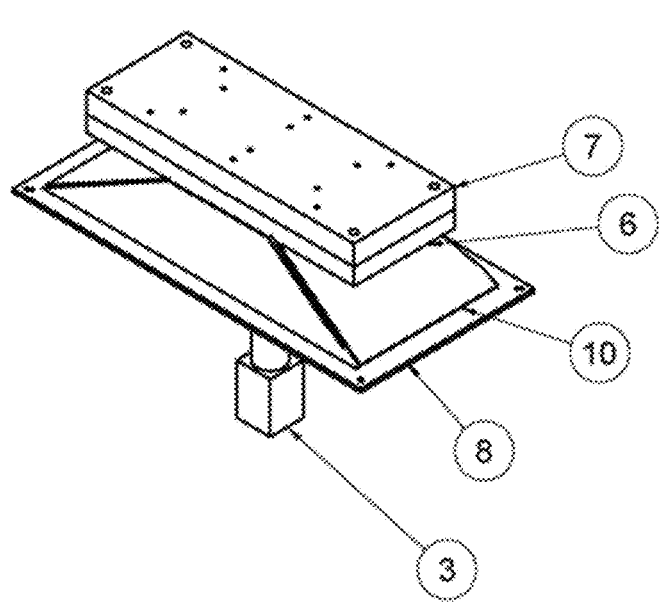
Figure 7:
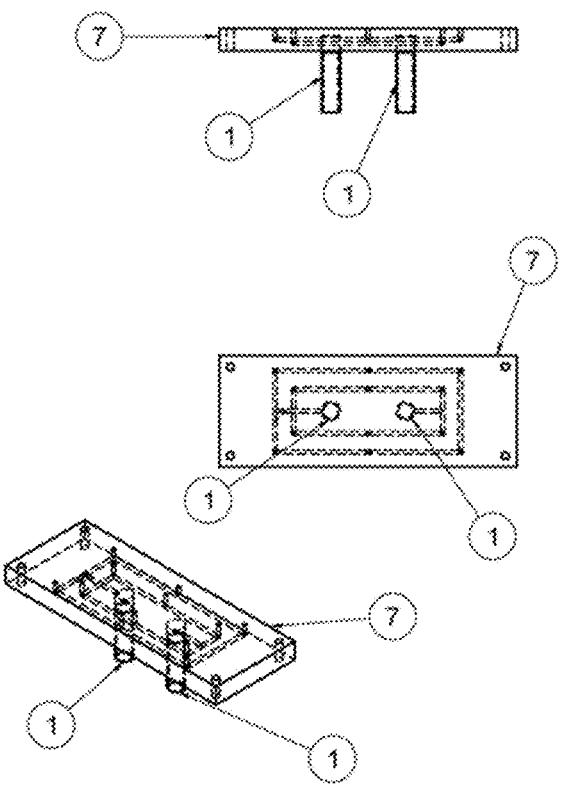

The vessel compartments (FIGS. 15 and 16) are printed at a defined distance, with the vessel compartments of the ascending and descending vessels running alternately below one another. One compartment each of the ascending vessel (2) and the descending vessel (3) are connected to each other by bridging vessels (6) and form the micro circuit (7) (FIGS. 15 and 16). This process is repeated until the individual module is filled. To print a tissue or an organ, a tissue module (FIG. 17) (8) is printed, which consists of several individual modules. The individual modules are printed flush next to each other on the printing plate, offset in their alignment (FIG. 7), resulting in a tissue module with a defined side length and thickness. The organ modules can be printed at the same time on different printers and connected to form larger tissue or organ units using an adhesive (eg fibrin glue) (FIG. 5).

In order to be able to connect the tissue modules to the body's circulatory system, a tissue termination module (8) (FIGS. 15 and 17) and a tissue connection module (9) (FIGS. 15 and 17) must preferably be printed.

The tissue closure module (8) consists of a tissue module in which the ascending and descending vessels in the individual modules taper upwards and thus close and are terminated with several cell layers (10).

The connection module (9) must preferably combine the individual vessels of the individual modules to form larger vessels, taking into account the anatomical and surgical specifications. The inflowing and outflowing vessels run at different levels to the connecting vessels (9). The ascending and descending vessels are again connected to each other by bridging vessels to supply the tissue (FIGS. 15,17).

General Description of the Printing Process (FIGS. 1-12)

In order to achieve an economical printing process, the tissue to be printed is preferably divided into individual tissue modules, which in turn are composed of individual modules. The tissue module consisting of the individual modules and the individual modules form a cross section from a defined level of the entire tissue or organ with its different cell types and vessels. This subdivision is done with the help of a specific algorithm. By printing the individual levels (tissue sections), a three-dimensional tissue is created again.

According to the specifications of the tissue module, the pressure plate with the supply openings is printed from a polymer.

The printing film is also printed from a biodegradable polymer and attached to the printing table together with the printing plate and inserted into the printing room.

The tanks for capillary inks, tissue inks and structure inks are filled and connected.

The required cell types are multiplied in an external, specially equipped and certified laboratory and pre-concentrated for the printing process and transported to the printer in the tanks.

The containers for the medium inlet and outlet are filled and the inlet and outlet hoses are connected to the corresponding connections on the printer table base. The inflow and outflow are supplied by a pump system, which has a flow and return. The printer room is also filled with medium, which can be kept constant via an inflow and outflow system. The printing process can now be started, the printing plate moves to its starting position.

First, the vessel connections are printed onto the printing film on the printing plate using the textured ink. The printer then prints layer by layer, forming the individual tissue areas and vessels layer by layer, and sinks into the medium of the printer room until the tissue module is complete. The printing process is programmed in such a way that a short rinsing process is initiated in recurring cycles after the tissue has reached a certain height in order to rinse out the excess and uncrosslinked cells. This rinsing process can take various forms. After a defined number of printing processes, the ascending branch is preferably flushed once, then after a further defined number of printing processes the descending branch. Always alternating until the tissue module is completely printed. The alternating rinsing process allows the incoming and outgoing vessels to be rinsed without overloading the vessels.

When the individual module has been printed, it can be easily detached from the printing table using the printing foil. The printed individual modules are assembled with an adhesive (e.g. fibrin glue) to form a complete tissue or organ. The inflowing and outflowing vessels of the individual modules are combined to form inflowing and outflowing larger vessels.

The tissue can continue to be supplied with medium via the arterial and venous circulation printed in the tissue and can mature in an incubator for several days before it is transplanted.

Individual modules using the example of the liver (FIGS. 15, 16, 17, 18):

The liver consists of about 1-1.5 million liver lobules with a diameter of 1-2 mm. Two vessels end in the liver, the hepatic artery, which supplies the tissue with oxygen and nutrients, and the portal vein, which transports the blood from the stomach and intestines with the absorbed nutrients and toxins. The veins that unite to form the vena cava and the bile duct go out of the liver.

Figure 15A:
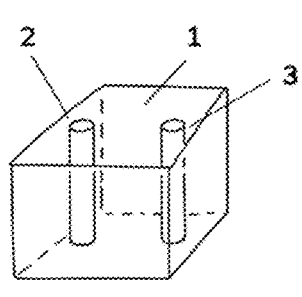
FIGS. 15A-15I are structures of a tissue module.
Figure 15B:
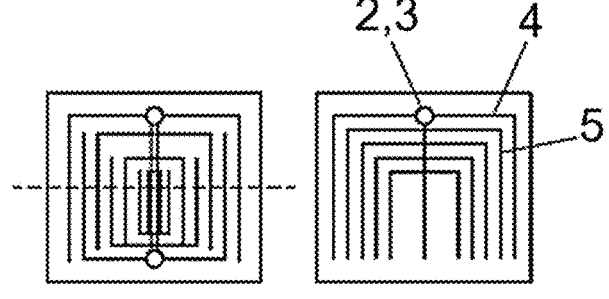
Figure 15C:
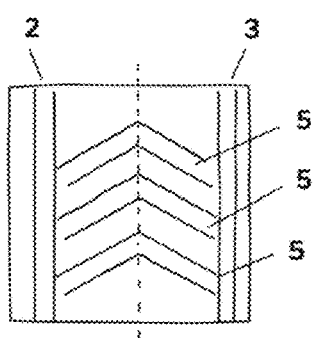
Figure 15D:
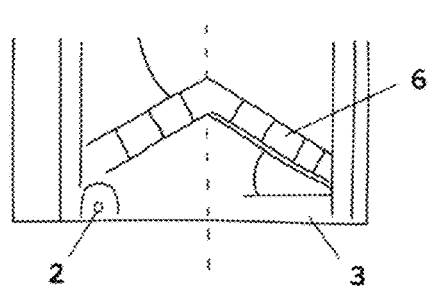

The individual module is formed here from the individual hexagonal liver lobules (1) (FIG. 17*a*) with a diameter of 2 mm. The liver lobules are arranged side by side in 5 rows and each 5 rows high (FIG. 15*d*). The arrangement of the liver lobules in the rows, which is offset by half a liver lobe every second row, allows them to interlock when forming organ modules.

The individual hexagonal liver lobules have 3 vessels (artery (2), portal vein (4), bile duct) in each corner and the vein (5) in the middle. All 4 vessels form a micro circuit again (FIG. 2).

The liver lobule is divided into 6 segments (6) for the individual corner vessels, through which the microcirculation flows and which form a vascular fan (7) (FIG. 4). The two supplying vessels, the artery and the portal vein, run parallel to each other in the microcirculation towards the vein. The vein comes towards you from the middle, it runs below the supplying vessels, so the three vessels form a triangle. The artery and portal vein are again connected to the vein with vascular bridges and form a microcirculation. The bile duct is located in the middle of the triangle of vessels.

Printing Process of a Liver Module (FIGS. 17, 18)

In order to achieve an economical printing process, the tissue to be printed is divided into individual tissue modules, which in turn are composed of individual modules. The tissue module consisting of the individual modules and the individual modules form a cross section from a defined level of the entire tissue or organ with its different cell types and vessels.

This single module is further subdivided into many consecutive levels (slices) using an algorithm. Each level then forms a two-dimensional print image with the different cell types and patterns. By printing these planes (slices), a three-dimensional tissue is created again.

According to the specifications of the liver module, the pressure plate with the supply openings is printed from a polymer. The supply openings are the supply and discharge vessels of the individual liver lobules (artery, portal vein, bile duct vein).

Likewise, the printing film is printed from a biodegradable polymer (preferably polyhydroxybutyrate, PHB) with the supply openings and attached to the printing table together with the printing plate and inserted into the printing room.

The containers for capillary inks, tissue inks and structure inks are filled. The tanks for the hepatocytes, endothelial cells, cholangiocytes and epithelial cells are connected.

The cell types required for the respective print are multiplied in advance by an external, specially equipped and certified laboratory and pre-concentrated for the printing process and transported to the printer in the respective tanks.

The containers for the medium inlet and outlet are filled and the inlet and outlet hoses are connected to the corresponding connections on the printer table base. The inflow and outflow are supplied by a pump system, which has a flow and return.

The printer room is also filled with medium, which can be kept constant via an inflow and outflow system.

The printing process can now be started, the printing plate moves to its starting position. All processes are organized by programmed algorithms, which in turn receive control signals from the printer and process them further.

The printer now prints level by level and forms the individual tissue areas layer by layer and sinks into the medium of the printer room until the tissue module is finished. The printing process is programmed in such a way that after the tissue has reached a certain pressure level, a brief rinsing process is initiated in order to flush out the excess and uncrosslinked cells. The pressure is programmed in such a way that the rinsing process is lengthened as the number of pressure levels increases, in order to transport the cells to be rinsed into the pressure chamber.

This flushing process can take place in various embodiments. In a preferred embodiment, the ascending branch is flushed once, then the descending branch after a further defined number of printing processes. Always alternating until the tissue module is completely printed. Due to the alternating rinsing process, the incoming and outgoing vessels can be rinsed without overloading the vessels.

After the liver module has been printed, it can be easily removed from the printing table using the printing foil.

When all the liver modules required for the tissue, as well as the tissue launch module and the tissue connection module have been printed, they are assembled with a glue (e.g., fibrin glue) to form a complete tissue or organ.

The tissue can continue to be supplied with medium via the arterial and venous circulation printed in the tissue and can mature in an incubator for several days before it is transplanted (FIG. 19).

EXAMPLES

Examples 1) to 4) correspond to the examples that have already been described under the chapter "Subject of the Invention". They are then supplemented by further exemplary embodiments.

The reference symbols listed in the examples relate in particular to the specific figures.

1) General Flow of a Print—Theoretical Basics and Preferred Versions

FIG. 15

The invention disclosed here describes a method for 3D printing of organs and tissues. Larger print areas are broken down into individual modules, printed independently of one another (on the same or on different printers) and then assembled and glued to the target organ or tissue (e.g., with fibrin glue). Inflowing and outflowing vessels of the individual modules are combined to form inflowing or outflowing main vessels. The individual module is preferably a cubic structure with a defined edge length.

A tissue or an organ may have the same structure, but they are not identical. Each individual, even within the same species, differs slightly from another. This is not only reflected in the size, but also in the individual development. The muscles of an athlete, for example, are much more capillarized than those of a non-athlete due to the higher oxygen requirement. The body adapts to the environmental conditions and is therefore never identical and experiences a constant build-up and breakdown.

For the tissue the function of it is therefore particularly important and not the exact anatomical reproduction of the patient's tissue. Therefore, a modular system is disclosed here, which enables the function of the tissue but has also been simplified and systematized to the extent that the 3D printing of the tissue can be carried out economically.

The basic building block of the tissue or organ is the cubic individual module (1) (FIG. 15a) with a defined side length. To supply the tissue, which can consist of one or more cell types and can therefore also form a functional tissue such as an organ, it is supplied on one side by an ascending vessel (2), which later forms the artery. The descending vessel (3) on the opposite side forms the vein. Smaller vessels (4) fan out from each of the vessels, which extend to the level of the opposite vessel on the other side and run parallel to one another (FIG. 15b). The smaller vessels (4) are connected to each other by bridging vessels (6), which later form the capillaries and close the "blood circuit" and form a microcirculation (7) (FIGS. 15c and 15d).

The microcirculation represents the smallest supply unit in the printed tissue. Here, the medium is fed via the ascending vessel (artery) (2) into a small vessel (4), which belongs to the ascending branch. The medium flows from the smaller vessel via the bridge vessels (6) into a smaller vessel (4) below, which belongs to the descending branch and flows into the descending vessel (3).

Since when printing the vessels with capillary ink, many cells are printed per drop and only the cells on the edge areas are able to network with the surrounding tissue, the excess cells have to be rinsed out. For this purpose and to supply the printed cells, after each completion of a micro circuit, one flushes with medium for a short time. With each rinsing process, the micro circuits below the last micro circuit are also rinsed and the cells supplied. The flow of medium flushes out the uncrosslinked cells. Horizontally running vessels are not optimal for this, which is why the printed vessels all run at an angle of 10 to 90 degrees to the printing plate.

The ascending and descending vessels (2 and 3) rise at an angle of 90°. The vascular compartments (5) can rise at an angle of 10-90°. Printing is ascending up to the middle of the individual module, then descending, so that the smaller vessels always run ascending to the printer plate. In this way, the excess cells can be rinsed out easily from the unfinished printed vessels. If a micro circuit (7) is closed, the medium can run off via the descending vessel (FIG. and 15f).

Figure 15E:
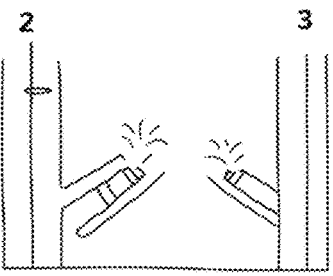
Figure 15F:
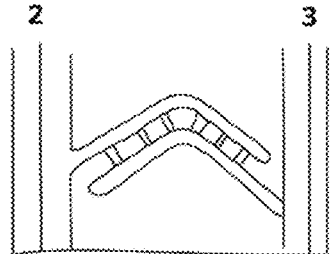
Figure 15H:
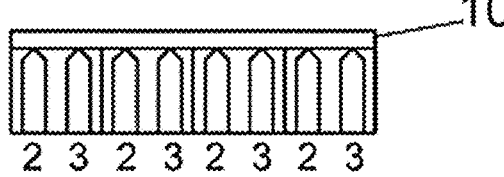
Figure 15G:
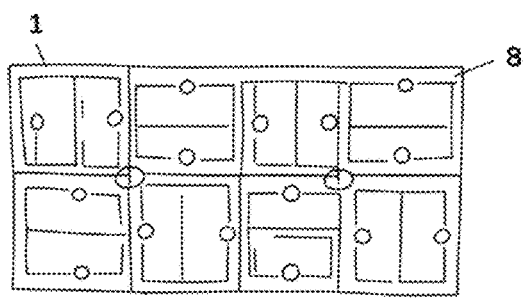
Figure 15I:
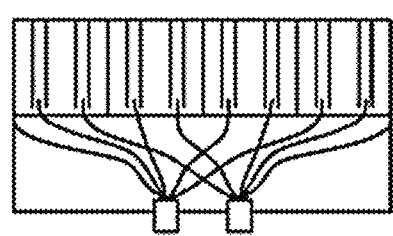

The vascular compartments are printed at a defined distance, with the vascular compartments of the ascending and descending vessels running alternately under one another. One vascular compartment each of the ascending vessel (2) and the descending vessel (3) are connected to each other by bridging vessels (6) and form the microcirculation (7) (FIG. 15d). This process is repeated until the individual module is filled. To print a tissue or an organ, a tissue module (8) consisting of several individual modules is printed. The individual modules are printed flush next to each other on the printing plate, offset in their orientation (FIG. 15g), resulting in a tissue module with a defined side length and thickness. The organ modules can be printed at the same time on different printers and connected to form larger tissue or organ units using an adhesive (e.g., fibrin glue) (FIG. 15e).

In order to be able to connect the tissue modules to the body's circulatory system, a tissue termination module (8) (FIG. 15g) and a tissue connection module (9) (FIG. 15h) must be printed.

The tissue closure module (8) consists of a tissue module in which the ascending and descending vessels in the individual modules taper upwards and thus close and are terminated with several cell layers (10).

The connection module (9) must preferably combine the individual vessels of the individual modules to form larger vessels, taking into account the anatomical and surgical specifications. The inflowing and outflowing vessels run at different levels to the connecting vessels (11). The ascending vessels and the descending vessels are again connected to each other by bridging vessels to supply the tissue.

2) General Description of the Printing Process

In order to achieve an economical printing process, the tissue to be printed is divided into individual tissue modules, which in turn are composed of individual modules. The tissue module consisting of the individual modules and the individual modules form a cross section from a defined level of the entire tissue or organ with its different cell types and vessels. This subdivision is done with the help of a specific algorithm. By printing the individual levels (tissue sections), a three-dimensional tissue is created again.

According to the specifications of the tissue module, the pressure plate with the supply openings is printed from a polymer.

The printing film is also printed from a biodegradable polymer and attached to the printing table together with the printing plate and inserted into the printing room.

The tanks for capillary inks, tissue inks and structure inks are filled and connected.

The required cell types are multiplied in an external, specially equipped and certified laboratory and pre-concentrated for the printing process and transported to the printer in the tanks.

The containers for the medium inlet and outlet are filled and the inlet and outlet hoses are connected to the corresponding connections on the printer table base. The inflow and outflow are supplied via a pump system, which has a forward and reverse flow. The printer room is also filled with medium, which can be kept constant via an inflow and outflow system. The printing process can now be started, the printing plate moves to its starting position.

First, the vessel connections are printed onto the printing film on the printing plate using the texture ink. The printer then prints layer by layer, forming the individual tissue areas and vessels layer by layer, and sinks them into the medium of the printer room until the tissue module is complete. The printing process is programmed in such a way that a short rinsing process is initiated in recurring cycles after the tissue has reached a certain height in order to rinse out the excess and uncrosslinked cells. This rinsing process can take various forms. After a defined number of printing processes, the ascending branch is preferably flushed once, then after a further defined number of printing processes the descending branch is flushed. This alternates until the tissue module is completely printed. The alternating rinsing process allows the incoming and outgoing vessels to be rinsed without overloading the vessels.

When the individual module has been printed, it can be easily detached from the printing table using the printing foil. The printed individual modules are assembled with an adhesive (e.g. fibrin glue) to form a complete tissue or organ. The inflowing and outflowing vessels of the individual modules are combined to form inflowing and outflowing larger vessels.

The tissue can continue to be supplied with medium via the arterial and venous circulation printed in the tissue and can mature in an incubator for several days before it is transplanted.

3) Individual Modules Using the Example of the Liver (FIG. 17)

The liver consists of about 1-1.5 million liver lobules with a diameter of 1-2 mm. Two vessels end in the liver, the hepatic artery, which supplies the tissue with oxygen and nutrients, and the portal vein, which transports the blood from the stomach and intestines with the absorbed nutrients and toxins. The veins then unite to form the vena cava and the bile duct go out of the liver.

The individual module is formed here from the individual hexagonal liver lobules (1) (FIG. 17a) with a diameter of 2 mm. The liver lobules are arranged side by side in 5 rows and each 5 rows high (FIG. 17b). The arrangement of the liver lobules in the rows, which is offset by half a liver lobe every second row, allows them to interlock when forming organ modules.

The individual hexagonal liver lobules have 3 vessels (artery (2), portal vein (4), bile duct) in each corner and the vein (5) in the middle. All 4 vessels again form a microcircuit (FIG. 17b).

The liver lobule is divided into 6 segments (6) for the individual corner vessels, through which the microcirculation flows and which form a vascular compartment (7) (FIG. 17d). The two supplying vessels, the artery and the portal vein, run parallel to each other in the microcircuit towards the vein. The vein comes towards you from the middle, it runs below the supplying vessels, so the three vessels form a triangle. The artery and portal vein are again connected to the vein with vascular bridges and form a microcircuit. The bile duct is located in the middle of the triangle of vessels.

4) Exemplary Printing Process of a Liver Module (FIGS. 17, 18)

In order to achieve an economical printing process, the tissue to be printed is divided into individual tissue modules, which in turn are composed of individual modules. The tissue module consisting of the individual modules and the individual modules form a cross section from a defined level of the entire tissue or organ with its different cell types and vessels.

This single module is further subdivided into many consecutive levels (slices) using an algorithm. Each level then forms a two-dimensional print image with the different cell types and patterns. By printing these planes (slices), a three-dimensional tissue is created.

According to the specifications of the liver module, the pressure plate with the supply openings is printed from a polymer. The supply openings are the supply and discharge vessels of the individual liver lobules (artery, portal vein, bile duct vein).

Likewise, the printing film is printed from a biodegradable polymer (preferably polyhydroxybutyrate, PHB) with the supply openings and attached to the printing table together with the printing plate and inserted into the printing room.

The containers for capillary inks, tissue inks and structure inks are filled. The tanks for the hepatocytes, endothelial cells, cholangiocytes and epithelial cells are connected.

The cell types required for the respective print are multiplied in advance by an external, specially equipped and certified laboratory and pre-concentrated for the printing process and transported to the printer in the respective tanks.

The containers for the medium inlet and outlet are filled and the inlet and outlet hoses are connected to the corresponding connections on the printer table base. The inflow and outflow are supplied by a pump system, which has a flow and return.

The printer room is also filled with medium, which can be kept constant via an inflow and outflow system.

The printing process can now be started, the printing plate moves to its starting position. All processes are organized by programmed algorithms, which in turn receive control signals from the printer and process them further.

The printer now prints layer by layer and forms the individual tissue areas layer by layer and sinks into the medium of the printer room until the tissue module is finished. The printing process is programmed in such a way that after the tissue has reached a certain pressure level, a brief rinsing process is initiated in order to flush out the excess and uncrosslinked cells. The pressure is programmed in such a way that the rinsing process is lengthened as the number of pressure levels increases, in order to transport the cells to be rinsed into the pressure chamber.

This flushing process can take place in various embodiments. In a preferred embodiment, the ascending branch is flushed once, then the descending branch after a further defined number of printing processes. Always alternating until the tissue module is completely printed. Due to the alternating rinsing process, the incoming and outgoing vessels can be rinsed without overloading the vessels.

After the liver module has been printed, it can be easily removed from the printing table using the printing foil.

When all the liver modules required for the tissue, as well as the tissue termination module and the tissue connection module are printed, they are assembled with a glue (e.g., fibrin glue) to form a complete tissue or organ.

The tissue can continue to be supplied with medium via the arterial and venous circulation printed in the tissue and can mature in an incubator for several days before it is transplanted.

5) An Extended Variant of the Printer Structure

The Printer Includes

Several printer heads with a number of nozzles for the droplet process and with one or more spatially controllable sources for electromagnetic waves, which lead to an energy input that can be modulated in terms of wavelength, intensity and frequency The modulated electromagnetic waves are used for the selective activation of cross-linking reactions A lockable reaction tray filled with medium with connections for changing the medium, taking samples and, after printing, optionally changing the supply route for medium or patient blood, the reaction tray can be removed from the printer and can function as an incubator A bottom plate located in the reaction tank with connections for the resulting vascular system, through which medium flows continuously or at intervals and serves to supply the printed tissue Multiple tanks for the required inks Various capillary inks, bio-inks and structured inks Structural areas (e.g., supporting structures, extracellular matrix or other non-cellular components, e.g., polyhydroxyalkanoates, fibrinogens, collagens, myelins, glycosamines, glycolipids, peptides, sugar molecules, fatty acids, lock-and-key molecules, organic and inorganic molecules for conduction, etc.)

Molecules with certain properties (e.g., molecules of various physiological properties, e.g., growth factors, transcription factors, receptor molecules, signaling molecules, RNA, DNA, differentiation molecules, etc.)

Homogeneous cell types (e.g., myocytes, liver cells, neurons, etc.)

Mixtures of heterogeneous cell types (e.g., endothelial cells, muscle cells) for the pressure of the vascular system The printer table can be raised and lowered during printing, optionally the printer head can be raised and lowered instead or both together.

6) Example Of Printed Tissue Maturation in Incubator

The incubator is used to advance the printed tissue or organ. Although a tissue complex with a high cell density has already been formed after printing, the cells have not yet reached their final tissue structure and differentiation. The tissue or organ is printed directly into a chamber that later serves as an incubator. Optionally, the tissue or the organ can also be transferred to another incubator. The incubator provides important parameters that are necessary for differentiation, for example chemical or molecular-biological substances or flow parameters.

The incubator can optionally be operated with nutrient medium and connected to the patient's bloodstream at a later point in time outside the body, or the incubator can be connected to the patient's bloodstream immediately after printing. Upon contact with the patient's blood, the necessary adult form and function or differentiation and growth factors reach the printed structures and the cells can adapt to the body.

7) Exemplary Build-Up of the Printer Head (FIG. 19)

The printer head consists of a first section for the droplet printing of bio inks, capillary inks and structured inks. The droplet process usually runs over piezo nozzles or bubble nozzles. The printing process is similar to the cyan/magenta/yellow/black/grey/light gray/light magenta/light cyan system of photo printers in terms of the sequence and the arrangement of the drops produced. Instead of the color inks there is the required number of bio-inks, capillary inks and structure inks.

In a second section, the printer head has one or more non-directional or directional sources for electromagnetic waves. In their entirety, the directional sources generate a selective energy source that can be modulated with regard to wavelength, intensity and frequency. UV lamps, light-emitting diodes, lasers or screens are generally used as sources for electromagnetic waves. Electromagnetic waves commonly used are ultraviolet light, visible light, and wavelengths in the infrared spectrum.

The functional units of the printer head for the droplet method and for the method for providing the electromagnetic waves can also be arranged separately from one another. Also, the printer head can be constructed from a series of modules of such units.

8) Another Alternative Structure of the Reaction Tank With Base Plate, Supply of Medium (FIGS. 1,2,3,4,5,6,7)

In the printer's pressure chamber is a printer table that can be moved up and down and has a number of connections for the medium to flow through the printed vascular structures.

Outside the pressure room, the ports are connected to an external system for maintaining specific cell culture parameters. These include temperature, pH value, $CO_2$ content, $O_2$ content, nutrients, growth factors, etc. Since the non-crosslinked cells within the printed vascular structures are also flushed out in the form of cell debris or as whole cells, the parameters of the medium flowing into the pressure chamber must preferably be checked and, if necessary, cleaned or exchanged.

During printing of the vascularized tissue, media is directed through the ports into the vascular structures printed on it. On the one hand, this serves to nourish the developing tissue and, on the other hand, to flush out the hollow structures of the vascular system. The medium enters the vascular structures through the connections of the printer table, flows through the vascularized tissue printed so far and seeps out again above on the side facing the printer head at the still open cavities of the vascular system. From there, the medium either flows passively back into the printer room or is actively removed from the printing surface during the printing process (e.g. rinsed or vacuumed).

During the printing process, the printer table lowers further and further into the printing space, so that the printed tissue is surrounded by the medium in the printing space. Approximately 1-5 mm of the top portion of the tissue protrudes from the media. Since the thiol-ene reactions are relatively insensitive to $O_2$, it is generally not necessary to fill the air-filled areas of the reaction tank with inert gas (e.g., nitrogen, argon).

9) Providing the Necessary Digital Information for the 3D Printer—Software

The digital data on the cellular structure of tissues and organs are obtained from medical imaging processes and programmed into 3D print data. These procedures include, for example, the MRT procedure or the "DISCO transparency" procedure. The methods for determining this data are known to those skilled in the art. A number of necessary modules for the economic pressure of required cell types as well as the required size and spacing of capillaries, venous and arterial vessels are calculated from this data using a special algorithm. For an economical print it is not necessary to reprint the biological structures in the original. The structure of individual modules has already been described under 1) to 4).

10) Novel Printer Software

The printer software processes the information about the tissues to be printed and passes this to the printer head and printer table for execution. In contrast to conventional 3D printer programming, both droplet technology (print pattern of specific inks and drop size) and, in the case of a directed source for electromagnetic waves, modulated laser technology (required wavelengths, energy intensities and frequencies, spatial control) are used here. combined and coordinated. A central role is played by the spatial and temporal coordination of the droplet release of specific ink types in the reaction trough of the printing plate with the tissue with the spatial and temporal provision of electromagnetic waves in an ink-specific wavelength, frequency and intensity that are necessary for their networking. The focus is on the selective crosslinking of endothelial cells and muscle cells within a drop of ink from a cell mixture to form vascular structures (section "Protective groups and photoinitiators used")

11) Maturation of A Printed Tissue and Organ Up to Transplantation

The incubator with tissue or organ has connections for the ex vivo connection to the patient's blood circulation or to a medium-supplying system. By incubating for a few hours to a few days, the cell structure of the 3D print is further differentiated. Important development factors are delivered to the cells, particularly through the connection of the vascular pressure system with the patient's bloodstream. The endothelial cells and muscle cells of the printed vascular structures also require a specific intravascular pressure through the blood or the medium and a specific flow rate for maturation.

During the maturation phase, it is possible to check specific physiological values via connections in the incubator and thus monitor the development of the organ or tissue. When the physiological values of the printed organ or tissue reach the physiological values of a natural organ within a certain range, it can be transplanted into the patient's body.

12) Exemplary Composition of the New Low-Viscosity Inks

The basic makeup of the ink consists of low-viscosity, short-chain crosslinking molecules, photoinitiators and cells. The short-chain crosslinking molecules have at least one, usually 2 or more, functional groups, which usually consist of allyl groups or thiol groups and undergo polymerization or addition reactions.

Crosslinking molecules that are frequently used are methacrylate-modified and thiol-modified molecules, eg methacrylate-modified or thiol-modified peptide chains, polyhydroxyalkanoates, or hyaluronic acids. The bio-inks and structured inks are either predominantly composed of methacrylate-modified molecules (radical polymerization or addition) or of a mixture of methacrylate-modified molecules with thiol-modified molecules (thiol-ene reactions).

The capillary inks, on the other hand, are usually made up of pure thiol-modified crosslinking molecules, which only crosslink at the edge areas of the drop in interaction with the allyl-modified crosslinking molecules of the bioinks and structured inks.

As a rule, photoinitiators are used that either work of wavelengths in the range of approx. 380 nm or with photoinitiators that are in the infrared range. Photoinitiators in the infrared range are stereo energy sources similar to multiphoton stereolithography (nonlinear multi-photon absorption), in which different energy sources must be superimposed in order to trigger a reaction.

When printing cells with selective factors (eg cleavable protecting groups for thiol groups), additional photoinitiators are used below 380 nm.

Examples of photoinitiators used are DAROCUR 1173, IRGACURE 2959 and 369, $(Ru(phen)_3/Iodine/(TMS)_3$ Si—H PIS) and Photoinitiator 183 from [1] Photoinitiators for IR excitations are H-Nu-IR 780 and H-Nu-IR 815. It has been found that a number of photoinitiators from the visible light range can also be activated by multiphotons.

13) Providing Cells Required for Printing

Cells for the novel 3D printing process disclosed herein can be provided in a variety of ways. The origin of the cells depends on the intended use of the tissue or organ printed with them.

The easiest way to generate cells is to use commercially available cell lines. With such cells, pressure parameters and cultivation parameters can be optimized, since one does not have to use the relatively expensive induced stem cells (iPS) or cells isolated from organs and tissues for these tests.

Another source of cells is the isolation of specific cell types from organs and tissues. In addition to animal cells for research, this process is also used in a variety of regenerative medicine, for example the isolation of intervertebral disc cartilage cells from prolapsed material from intervertebral disc operations. The prolapse material is dissolved and the cells are isolated from it, multiplied and used, among other things, in the 3D printing of tissues.

Arguably the most challenging source of cells is the generation of induced stem cells (IPSs). Various established working groups have procedures for this. iPS cells are required for printing human tissues and organs to be subsequently implanted in the human body. But these cells and the structures printed from them can also be used in cell culture as test material for individualized medication. iPS cells are usually grown from donor skin cells. The skin cells are differentiated into iPS cells, multiplied and differentiated into the cell types required for printing. These processes are not yet well established for widespread use, but represent the future in the manufacture of human autologous implants for organs and tissue.

Other sources of cell material are cell lines grown for specific purposes, which have usually been modified in various ways (eg on a DNA-based, RNA- or protein-based basis).

In principle, any cell type (primary or cell line) can be grown and printed with the method disclosed here.

13) Exemplary Inks for Printing With Cells Containing a Selective Factor (FIGS. 13, 14)

One way of crosslinking capillary inks only in the edge area is the use of cell mixtures of endothelial cells and muscle cells, which are selectively crosslinked with each other within a drop. In order to be selectively activated by a directed laser beam, these cell types require a specific selective factor. This selective factor is, for example, a cleavable protecting group on a thiol functional group located on the cell membrane of the cell type in question. By using different protective groups that can be cleaved at different wavelengths, the different cell types can be separated from one another in their cross-linking reaction. Typically, the capillary ink in this application consists of protected thiol-modified crosslink molecules anchored to the cell membrane and free thiol-modified protected molecules in the ink. In addition, there are allyl modified molecules in the ink to enable a thiol-ene crosslinking reaction.

14) Exemplary Structure of the Inks and Selective Factor (FIGS. 13, 14)

The light-dependent thiol-ene reaction takes place selectively within the spatial cross-linking area defined by the laser via selective factors. These selective factors consist, for example, of light-cleavable protecting groups that block the thiol groups. Due to their different molecular structure, these protective groups can be cleaved by different wavelengths of light. Protecting groups are selected that do not overlap in their excitation spectrum.

In order to selectively crosslink only certain cell types from a mixture in an area hit by the laser, but not others, the protective groups on the thiol groups of the cells in question must be cleaved. Thus, only these cells and these crosslinking molecules are accessible to a thiol-ene reaction. In this example, the thiol-ene crosslinking reaction is then started by a photoinitiator whose excitation spectrum is above the wavelength of all the protective groups used, so as not to accidentally split them (see examples below).

15) Print of the Vascular System With Cells Containing a Selective Factor

Since the diameter of the fine capillaries between the arteries and veins is only a few micrometers, but the drops in the droplet process are larger, the inner single-layer ring of endothelial cells is selectively crosslinked from a drop of a cell mixture. The ring of muscle cells surrounding this ring is also selectively crosslinked from the cell mixture. For this purpose, the endothelial and muscle cells carry protective groups that can be cleaved at different wavelengths as a selective factor (see examples below).

After selective cleavage of the protective groups on the corresponding cell type, the thiol-ene reaction can take place in the deprotected cells. First, a laser beam 1 in the drop deprotects approx. 5-7 endothelial cells and the protected thiol-modified crosslinking molecules lying between them to form a ring-shaped structure and then they are ring-linked with one another by a laser beam 2. Laser beam l is used to stimulate a photoinitiator and is above the wavelength of laser beams 1 and 3.

This creates a single layer of endothelial ring with an inner diameter of about 10 microns, the inner surface of which consists of non-crosslinked, blocked cells. Subsequently, the outer muscle cells adjacent to the endothelial ring and protected thiol-modified crosslinking molecules are deprotected by a laser beam 1 and crosslinked with one another with a laser beam 2 to form an outer ring. While laser beams 1 and 3 split the corresponding protective groups at different wavelengths, laser beam 2 activates a photoinitiator that starts the thiol-ene reactions.

The uncrosslinked cells inside the capillaries are destroyed by a laser beam of higher energy (laser beam 4) and the resulting cell debris is flushed out by the inflowing medium.

16) Protecting Groups and Photoinitiators Used in Inks With Selective Factors (FIGS. 13, 14)

While the type of reaction for the cross-linking of inks with homogeneous cell types can be chosen freely and proceeds unselectively, the various cell types with heterogeneous inks have thiol-ene—reaction partners with a specific protective group that can be cleaved at the corresponding wavelength. The curves of the necessary activation energies must not overlap (FIG. 13).

The following UV-cleavable protecting groups were used to cross-link the endothelial cells and the muscle cells surrounding them:

325 nm: (7,8-bis(carboxymethoxy)coumarin-4y1) methoxycarbonyl for muscle cells 400 nm: α carboxy-4methoxy-2-nitrobenzyl for endothelial cells (Source: wavelength-selective photolabile protecting groups for thiols, Nico Kotzur, 2009)

First, the protecting group is cleaved with the longer required wavelength to avoid inadvertently activating the other protecting group. For the actual thiol-ene reaction, a photo initiator (Ru(phen)$_3$/iodine/(TMS)$_3$ Si—H PIS) is used, whose excitation spectrum is at 532 nm in order not to inadvertently cleave the underlying protective groups. The photoinitiator 183 [1] which is excited at 473 nm, can also be used.

In a first step, the protective group on the thiol groups of the endothelial cells is split off at 400 nm (laser beam 1). In this area, the thiol groups of the muscle cells are still protected. Then the photoinitiator is activated at 532 nm and a thiol-ene reaction is triggered at the deprotected groups (laser beam 2). Due to the spatial guidance of the two consecutive laser beams (first 400 nm, then 532 nm), 5 to 12 endothelial cells are usually networked with each other in a ring.

In a second step, the protective groups on the thiol groups of the muscle cells are split off at 325 nm Laser beam 3). Since the spatial guidance of the laser beams for the area of the endothelial cells (400 nm and 532 nm) does not hit the area of the muscle ring surrounding the endothelial cells, the endothelial cells of the cell mixture are still present there with protective groups and can participate in the thiol-ene reaction of the deprotected thiol groups of the muscle cells do not participate. The activation of the photoinitiator at 532 nm then crosslinks the muscle cells in the ring (laser beam 2).

In this way it can be ensured that predominantly only the desired cell type is incorporated into the corresponding structure.

Additional protective groups for thiol groups are available for other selective factors that are required (FIG. 13), e.g., the group which can be cleaved at 436 nm ((7bis(carboxymethyl)amino)-coumarin-4-yl) methoxycarbonyl). The cross-linking process is analogous to that described above. (Source: wavelength-selective photolabile protecting groups for thiols, [4])

The non-crosslinked cells inside the capillaries are destroyed by a laser beam 4 of higher energy and the debris is flushed out of the medium.

17) Exemplary Production of Autologous Patient Cells With a Selective Factor

The cells taken from the patient (e.g., skin cells) are converted into induced stem cells (iPS), multiplied, split into individual fractions and then differentiated into the required cell types. This preparation takes place independently of the printing process and is only mentioned here as an example to describe the way to real 3D organs. This process can take weeks to months depending on the complexity of the organ to be printed. Once the required cell lines have been produced, they can be frozen and stored until printing is due. Frozen cells can be thawed, hybridized with the selective factor, and printed. An incubation period of 24 hours after thawing in the cell culture and subsequent hybridization with their specific selective factor is gentler on the cells.

Typically, the selective factor is linked to an anchor molecule to tie down in the cell membrane. The anchor molecules used can usually be used universally for all cell types. Surprisingly, perfluorinated anchor molecules have been shown to be the most effective. Experience has shown that these molecules bind to 100% of the cells involved within 2 minutes. However, lipophilic molecules, peptides, ions or antibodies can also function as anchor molecules.

18) Preparation of Selective Factor Cells for Printing

Shortly before printing, the cells of the capillary system are hybridized with their specific selective factor: The endothelial cells and muscle cells used are first prepared separately for printing in the cell culture and hybridized with their respective selective factor. They are then brought together in the capillary inks.

Further Comments on the Figures

FIG. 1

FIG. 1: Exemplary Schematic Printer Structure and Function

The basis of the invention is a conventional photorealistic piezo printer.

Newly disclosed are modifications of the ink supply (1-5) and the construction of the printer table (12, 13, 14, 15).

The printer consists of the ink supply units (1-5), the piezo printer head (15), the printer table (13), the print chamber (14) filled with medium and the motor of the print table (12). In addition, there is a medium tank (8) for supplying the tissue with supply hoses (9) and a waste tank (11) and medium-removing hoses (10) on the printer.

The individual components are surrounded by a housing (6). Outside the case is the central control unit/computer/software (7) which communicates with components 1-5, 15 and 12 (dashed lines).

FIGS. 2-7

FIGS. 2-7: Exemplary Structure of the Printer Table and How it Works

In the following a new system of a printer table is disclosed. The printing table essentially consists of 5 parts:

A pressure plate (7), a printer table (6) with supply connections, which can be lowered in the pressure chamber by means of a stepping motor (3) and a micrometer screw (2).

The pressure plate (7) is printed individually for the organ or organoid using a 3D printer (FDM, SLS, SLM SLA, or other printer), since the openings for supplying the tissue can be different. The difference can be due to the positioning, number and diameter.

The pressure plate (7) made of a biocompatible polymer has the connection openings for the medium inlet and outlet (1), from which a line system extends individually for the tissue within the plate and opens into several openings for the supply of the tissue on the surface . The openings can be positioned differently and also have different diameters. The vessels for supplying the tissue are then printed onto these openings.

The printing plate is screwed onto the printing table (6), the printing table consists of a magnetic material and has bores in which the connectors (1) for the inlet and outlet of the medium are plugged. Below the printing plate is the printing table foot (5), in which the pin of the micrometer screw is fitted with low friction, as well as the connections (eg Luer connections) for the inlet and outlet (1) of the medium. In a preferred embodiment, the connection pieces for the inlet and outlet on the upper side of the printing table foot (5) are designed as pins and fit exactly into the holes in the printing table. A magnetic plate is attached to the top of the printing table base. The power of the magnet connects the printing table and the printing table base and thus establishes a connection between the connections for the inflow and outflow to the printing plate. Sealing rings in the bores prevent the medium from leaking out. The printed tissue, including the printing plate and printing table, can also be easily separated from the other permanently installed components via the magnetic connection and plugged into another supply unit.

Using the pin of the micrometer screw (2) and the stepping motor (3), the printing table including the printing plate can be lowered into the printing space (space above the silicone mat). The pressure chamber consists of a base plate (8) and a wall (9) made of stainless steel, for example, and thus forms a space that can be filled with medium via feeds. The printed tissue is lowered into this medium to nourish it and protect it from drying out. By lowering the printed areas, the print level remains at a constant height. An overflow prevents overflow by displacement of the medium.

In a special embodiment, there is a silicone mat (10) for sealing above the base of the printer table (5).

This is stretched over the printer table foot (5), whereby the spigots for the inlet and outlet remain free and reach over the edge of the base plate of the printing room. By screwing the pressure chamber wall (9) onto the base plate for the pressure chamber (8), the pressure chamber is sealed and the underside of the pressure table foot is separated from the pressure chamber with the pin of the micrometer screw. Due to the high flexibility of the silicone mat, the up and down movement of the printing table is still possible without any problems.

In a further embodiment, instead of the silicone mat, a seal is fitted between the pin of the micrometer screw (2) and the base plate for the pressure chamber (8) to seal the pressure chamber (eg mechanical seal).

In other embodiments, other constructs can be used to seal the pressure space.

FIG. 8

FIG. 8: Exemplary Structure of the Printer Head Supply Unit and How it Works

In the print head supply unit newly disclosed here, the cultivated cells are pumped from the cell tank (2) via a pump (4) into the cell concentrator (6), in which the cell concentration is increased and excess medium is discharged (9). A defined cell concentration is passed on via a cell counter (8) to a mixing unit (7) into which the ink concentrate is also introduced. The ink concentrate is conveyed from the reservoir (1) to the mixing unit (7) in a defined volume by a pump with a measuring unit (5). In this mixing unit (7), the ink for the printer heads is mixed according to specifications from the printing program and fed via a control cell counter into the hose leading to the piezo printer head (12).

The number of printer head supply units depends on the number of bio-inks required and can vary.

The printhead power unit is both controlled by the printer's algorithm to mix the required ink composition and has a number of sensors that provide the printer algorithm with information about the properties of the inks currently being mixed, to which the algorithm reacts.

Figure 9:
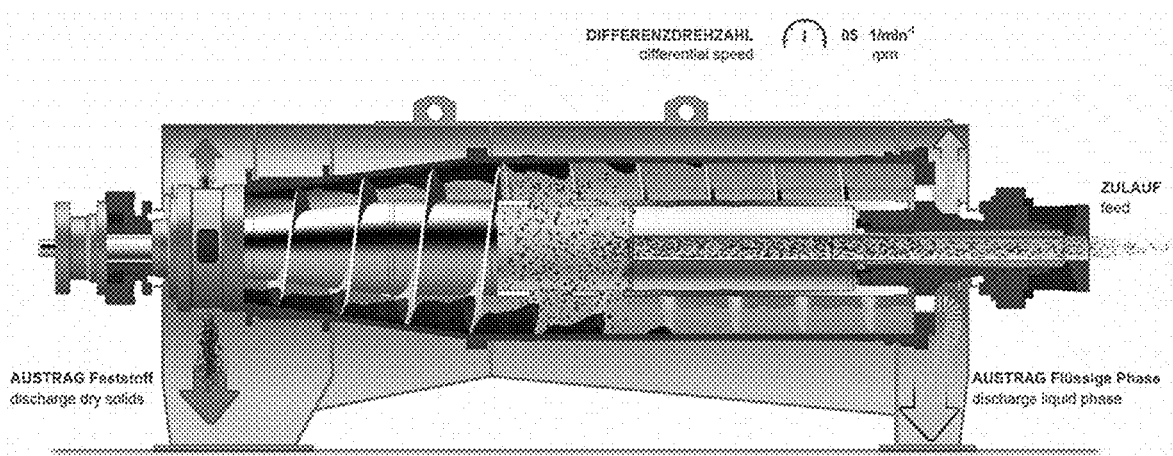
FIGS. 9 and 10: Preferred designs of the cell concentrator (6) for concentrating the cells using a decanter.
Figure 10:
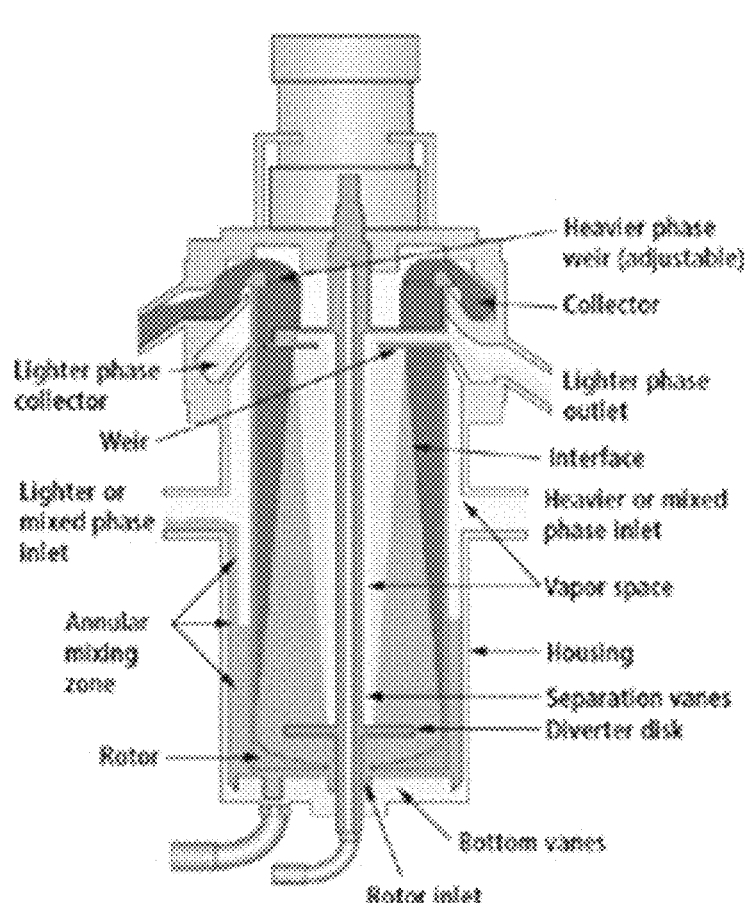

FIGS. 9 and 10

FIGS. 9 and 10: Preferred Designs of the Cell Concentrator (6) for Concentrating the Cells Using a Decanter To concentrate the cells, the following methods, which are characterized by permanent operation, are preferably used as the cell concentrator (6). The cells are concentrated by reducing the liquid phase, the medium. The solid and liquid phases can be separated either by centrifugal force or by filter properties.

In these designs, a flow-through centrifuge or a decanter is used to concentrate the cells. Both systems work on the same principle using centrifugal force.

In a centrifuge, the solid and liquid phases are separated with the help of centrifugal acceleration. In the rotating bowl of the centrifuge, the solid particles, which are denser and therefore heavier than the liquid, move outwards using centrifugal force. They form a sediment on the inner wall of the centrifuge bowl.

The decanter bowl has a cylindrical-conical shape and rotates at a speed that is tailored to the separation task in question. In the bowl, the product reaches full peripheral speed and forms a cylindrical ring on the bowl of the centrifuge. Due to the higher density, the solids contained in the product settle on the inner wall of the drum under the influence of centrifugal force. The length of the cylindrical part and the cone angle of the conical part of the bowl can be adapted to the respective separation task during manufacture of the decanter.

FIGS. 11 and 12

FIGS. 11 and 12: Preferred Designs of the Cell Concentrator (6) for Concentrating the Cells Through Dynamic Filtration In cross-flow microfiltration, the medium containing the cells flows over the filter membrane during the filtration process, so that there are two main flow directions orthogonal to one another. The main flow directions are the filter flow through the filter membrane and the overflow parallel to the filter membrane. The build-up of the filter cake during the filtration process is counteracted by the overflow of the suspension, so that the cell concentrate can flow off. The effectiveness of the filter property is variable due to the number of pores and pore size in the filter membrane. Hollow fibers (capillary membranes or also called hollow fibers) are particularly suitable for this purpose, and their performance is further enhanced by the pinch effect . A typical hollow fiber has an inner diameter of about 1.5 mm (3.0 mm to 0.1 µm possible) and a pore size of 200 to 5 nm (2000 nm to 1.0 nm possible). Depending on the application, hundreds to thousands of capillaries are combined in modules and cast (hollow fiber modules). With the aid of a circulation pump, the unfiltered product is circulated through the capillaries until the turbidity in the retentate is so concentrated that it needs to be emptied and cleaned . (Ripperger 1992), (Melin & Rautenbach 2007).

FIG. 13 selective factors—cleavable protecting groups for thiol groups at the wavelengths of 325 nm, 400 nm and 436 nm (source: wavelength-selective cleavable photolabile protecting groups for thiols, [4])

FIG. 14

Cells with selective factor. Light cells show endothelial cells, dark cells show muscle cells. Both cell types are present as a mixture in a capillary ink drop and can be selectively activated by 2 laser beams with different wavelengths for the cross-linking reaction.

FIG. 15

FIG. 15: Structure of a Tissue Module

The basic building block of the tissue or organ is the cubic individual module (1) (FIG. 15a) with a defined side length. To supply the tissue, which can consist of one or more cell types and can therefore also form a functional tissue such as an organ, it is supplied on one side by an ascending vessel (2), which later forms the artery. The descending vessel (3) on the opposite side forms the vein. Smaller vessels (4) fan out from each of the vessels, which extend to the level of the opposite vessel on the other side and run parallel to one another (FIG. 15b). The smaller vessels (4) are connected to each other by bridging vessels (6), which later form the capillaries and close the "blood circuit" and form a microcirculation (7) (FIGS. 15c and 15d).

The microcirculation represents the smallest supply unit in the printed tissue. Here, the medium is fed via the ascending vessel (artery) (2) into a small vessel (4), which belongs to the ascending branch. The medium flows from the smaller vessel via the bridge vessels (6) into a smaller vessel (4) below, which belongs to the descending branch and flows into the descending vessel (3).

Since when printing the vessels with capillary ink, many cells are printed per drop and only the cells on the edge areas are able to network with the surrounding tissue, the excess cells have to be rinsed out. For this purpose and to supply the printed cells , after each completion of a micro circuit, it is flushed with medium for a short time. With each rinsing process, the micro circuits below the last micro circuit are also rinsed and the cells supplied. The flow of medium flushes out the uncrosslinked cells. Horizontally running vessels are not optimal for this, which is why the printed vessels all run at an angle of 10 to 90 degrees to the printing plate.

The ascending and descending vessels (2 and 3) rise at an angle of 90°. The vascular compartments (5) can rise at an angle of 10-90°. Printing is ascending up to the middle of the individual module, then descending, so that the smaller vessels always run ascending to the printer plate. In this way, the excess cells can be rinsed out easily from the unfinished printed vessels. If a micro circuit (7) is closed, the medium can run off via the descending vessel (FIG. and 15*f*).

The vascular compartments are printed at a defined distance, with the vascular compartments of the ascending and descending vessels running alternately under one another. One vascular compartment each of the ascending vessel (2) and the descending vessel (3) are connected to each other by bridging vessels (6) and form the microcirculation (7) (FIG. 15*d*). This process is repeated until the individual module is filled. To print a tissue or an organ, a tissue module (8) consisting of several individual modules is printed. The individual modules are printed flush next to each other on the printing plate, offset in their orientation (FIG. 15*g*), resulting in a tissue module with a defined side length and thickness. The organ modules can be printed at the same time on different printers and connected to form larger tissue or organ units using an adhesive (eg fibrin glue) (FIG. 15*e*).

In order to be able to connect the tissue modules to the body's circulatory system, a tissue termination module (8) (FIG. 15*g*) and a tissue connection module (9) (FIG. 15*h*) must preferably be printed.

The tissue closure module (8) consists of a tissue module in which the ascending and descending vessels in the individual modules taper upwards and thus close and are terminated with several cell layers (10).

The connection module (9) must preferably combine the individual vessels of the individual modules to form larger vessels, taking into account the anatomical and surgical specifications. The inflowing and outflowing vessels run at different levels to the connecting vessels (11). The ascending vessels and the descending vessels are again connected to each other by bridging vessels to supply the tissue.

FIG. 16

FIG. 16: Flushing of the Resulting Capillaries With Medium

The printing process is programmed in such a way that a short rinsing process is initiated in recurring cycles after the tissue has reached a certain height in order to rinse out the excess and uncrosslinked cells. This rinsing process can take various forms. After a defined number of printing processes, the ascending branch is preferably flushed once, then after a further defined number of printing processes the descending branch. Always alternating until the tissue module is completely printed. The alternating rinsing process allows the incoming and outgoing vessels to be rinsed without overloading the vessels.

FIG. 17

FIG. 17: Liver—Organ Module

Individual Modules Using the Example of the Liver

The liver consists of about 1-1.5 million liver lobules with a diameter of 1-2 mm. Two vessels end in the liver, the hepatic artery, which supplies the tissue with oxygen and nutrients, and the portal vein, which transports the blood from the stomach and intestines with the absorbed nutrients and toxins. The veins that unite to form the vena cava and the bile duct go out of the liver.

The individual module is formed here from the individual hexagonal liver lobules (1) (FIG. 17*a*) with a diameter of 2 mm. The liver lobules are arranged side by side in 5 rows and each 5 rows high (FIG. 17*c*). The arrangement of the liver lobules in the rows, which is offset by half a liver lobe every second row, allows them to interlock when forming organ modules.

The individual hexagonal liver lobules have 3 vessels (artery (2), portal vein (4), bile duct) in each corner and the vein (5) in the middle. All 4 vessels again form a microcirculation (FIG. 17*b*).

The liver lobule is divided into 6 segments (6) for the individual corner vessels, through which the microcirculation flows and which form a vascular compartment (7) (FIG. 17*d*). The two supplying vessels, the artery and the portal vein, run parallel to each other in the microcirculation towards the vein. The vein comes towards you from the middle, it runs below the supplying vessels, so the three vessels form a triangle. The artery and portal vein are again connected to the vein with vascular bridges and form a microcirculation. The bile duct is located in the middle of the triangle of vessels.

FIG. 18

Superimposition of individual printed liver—organ modules

FIG. 19

FIG. 19: Exemplary Structure of an Incubator

The tissue incubator consists of a medium-filled tub (1) with a cover (2) to be placed on top. A foot (3) is permanently installed on the bottom of the tub, on which a printer table foot (5) of the same construction is exchangeably attached. The supply and discharge medium hoses (4) to the printer table base are routed through openings in the incubator vessel. The printer table including the printing plate, printing film and printed tissue is placed on the pins of the printer table base (without silicone membrane) by means of magnetic force.

Figure 20:
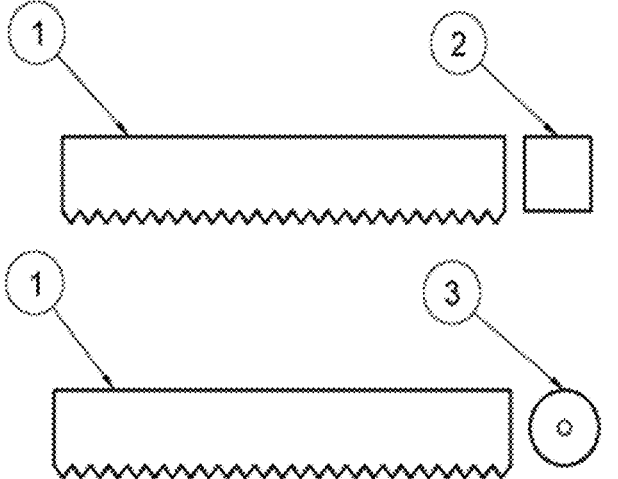
FIGS. 20 and 21: Exemplary structure of a printer head with non-directional and directional source of electromagnetic radiation
Figure 21:
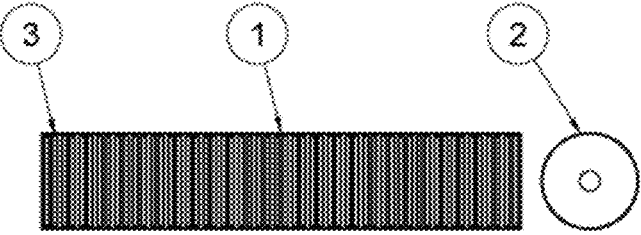

FIGS. 20 and 21

FIGS. 20 and 21: Exemplary structure of a printer head with non-directional and directional source of electromagnetic radiation.

CITATIONS

[1] Xiao, Pu et al. "Visible light sensitive photo initiating systems: Recent progress in cationic and radical photopolymerization reactions under soft conditions." Progress in Polymer Science 41 (2015): 32-66.

[2] Ripperger, S. Microfiltration with membranes. Fundamentals, processes, applications. Mikrofiltration mit Membranen. Grundlagen, Verfahren, Anwendungen. Germany: N. p., 1992. Web.

[3] T Melin, R Rautenbach (2007) Stoffaustausch an Membranen. In: Membranverfahren. VDI-Buch. Springer, Berlin, Heidelberg. https://doi.org/10.1007/978-3-540-34328-8_4

[4] Nico Kotzur (2009) Wellenlangenselektiv abspaltbare photolabile Schutzgruppen für Thiole; Logos Verlag Berlin GmbH, ISBN 3832522786, 9783832522780

[5] Yu, Yin et al. "A Hybrid Bioprinting Approach for Scale-Up Tissue Fabrication." Journal of Manufacturing Science and Engineering-transactions of The Asme 136 (2014): 061013.

[6] Kolesky, David B. et al. "Bioprinting: 3D Bioprinting of Vascularized, Heterogeneous Cell-Laden Tissue Constructs (Adv. Mater. 19/2014)." Advanced Materials 26 (2014): 2966-2966.

[7] Lee, Jung-Seob et al. "3D printing of composite tissue with complex shape applied to ear regeneration." Biofabrication 6 2 (2014): 024103

The invention claimed is:

1. A 3D printing process for the production of tissues and organs having vascular structures by means (a) a droplet printer for photorealistic high-resolution prints and (b) a device for applying electromagnetic waves comprising:

providing at least one bio-ink and one capillary ink with cells and cross-linking molecules in the droplet printer;

placing at least one drop of the bio-ink and the capillary ink on one reaction plane;

bringing the electromagnetic waves into contact with the crosslinking molecules in these drops at the reaction level; and activating of the cross-linking molecules by means of non-directional or directed movements of the electromagnetic waves in the drops, whereby cross-linked structures are formed and vascular structures are thus obtained; and wherein the capillary inks crosslink or form a layer only in the edge area of the drop at a border to drops of the bio-ink such that a cavity for the vascular structures is formed, wherein the crosslinking or layer-forming reactions in the edge area of capillary ink droplets are caused by components in the inks without requiring an addition of a selective factor during printing, wherein the capillary ink comprises endothelial cells and at least one of crosslinkable molecules, layer forming molecules, or a combination thereof, and

wherein after a cross-linked structure or layer structures have reached a certain height cross-linking molecules, unbound molecules and cells that are non-crosslinked or unbound are eliminated in recurring cycles.

2. The method according to claim 1, characterized in that the drop size is between 1 fl (femtoliter) and 1 μl (microliter).

3. The method according to claim 1, characterized in that reactions in the edge area of the capillary inks are caused by: thiolene reactions, cycloadditions, nucleophilic ring openings, self-assembly of molecules and particles, or selective factors on the cells of the capillary inks and/or bioinks.

4. The method according to claim 1, characterized in that the bioinks include molecules that support the physiology of the printed tissue or organ.

5. The method according to claim 1, characterized in that the bioinks contain growth factors, transcription factors, signaling molecules, marker molecules and/or target molecules for later key-lock reactions.

6. The method according to claim 1, characterized in that culture medium or blood flows through the printed vascular structures during printing.

7. The method according to claim 1, characterized in that the reaction plane is positioned in a bioreactor, which is connected to a blood circuit, during or after the end of a pressure of the blood circuit.

8. The method according to claim 1, characterized in that the device for applying the electromagnetic waves is a UV lamp, a diode, a screen or a laser beam device.

* * * * *